(12) United States Patent
Akiyama

(10) Patent No.: US 11,771,351 B2
(45) Date of Patent: *Oct. 3, 2023

(54) SENSOR AND METHOD FOR MANUFACTURING SENSOR

(71) Applicant: TERUMO KABUSHIKI KAISHA, Tokyo (JP)

(72) Inventor: Takeshi Akiyama, Chuo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 881 days.

This patent is subject to a terminal disclaimer.

(21) Appl. No.: 16/692,785

(22) Filed: Nov. 22, 2019

(65) Prior Publication Data

US 2020/0113494 A1 Apr. 16, 2020

Related U.S. Application Data

(63) Continuation of application No. PCT/JP2018/018181, filed on May 10, 2018.

(30) Foreign Application Priority Data

Jul. 5, 2017 (JP) .................................. 2017-132085

(51) Int. Cl.
*A61B 5/1473* (2006.01)
*A61B 5/145* (2006.01)
(Continued)

(52) U.S. Cl.
CPC .......... *A61B 5/1473* (2013.01); *A61B 5/1451* (2013.01); *A61B 17/3468* (2013.01);
(Continued)

(58) Field of Classification Search
CPC .............. A61B 5/14503; A61B 5/1451; A61B 5/14532; A61B 5/14546; A61B 5/1459;
(Continued)

(56) References Cited

U.S. PATENT DOCUMENTS 5,165,407 A * 11/1992 Wilson .................... C12Q 1/006
600/347
2002/0026195 A1 * 2/2002 Layne ................... A61F 2/4601
606/92
(Continued)

FOREIGN PATENT DOCUMENTS

EP 0320109 A1 * 6/1989 ........... A61B 5/6848
JP 2001-321439 A 11/2001
(Continued)

OTHER PUBLICATIONS

Machine translation of Sorimoto (JP 2016059427) taken from Global Dossier (Year: 2014).*
(Continued)

*Primary Examiner* — Tse W Chen
*Assistant Examiner* — Alice Ling Zou
(74) *Attorney, Agent, or Firm* — Foley & Lardner LLP

(57) ABSTRACT

A sensor includes: a tubular needle member that includes a side wall and defines a hollow portion; and a linear detection member located in the hollow portion. The side wall of the needle member includes a thick portion that is thicker than another portion of the side wall in a cross-section of the needle member, and wherein the thick portion protrudes toward the hollow portion.

10 Claims, 15 Drawing Sheets

(51) Int. Cl.
*A61B 17/34* (2006.01)
*A61B 5/1486* (2006.01)

(52) U.S. Cl.
CPC ....... *A61B 5/14532* (2013.01); *A61B 5/14865* (2013.01); *A61B 2560/063* (2013.01); *A61B 2562/12* (2013.01)

(58) Field of Classification Search
CPC .. A61B 5/1473–14735; A61B 5/14865; A61B 5/6848–6849; A61B 17/3417; A61B 17/3468; A61B 2560/063; A61B 2560/066; A61B 5/14514; A61B 5/14535; A61B 5/14539; A61B 5/14542; A61B 2017/3454; A61B 55/14514; A61B 17/3421; A61B 17/3454; B21G 1/08
See application file for complete search history.

(56) References Cited

U.S. PATENT DOCUMENTS

| | | | |
|---|---|---|---|
| 2003/0100821 A1 | 5/2003 | Heller et al. | |
| 2003/0225361 A1* | 12/2003 | Sabra | A61B 5/6849 604/19 |
| 2013/0245412 A1* | 9/2013 | Rong | A61B 5/14532 600/347 |
| 2013/0281802 A1* | 10/2013 | Matsumoto | A61B 5/150267 600/309 |
| 2015/0313521 A1* | 11/2015 | Say | A61B 5/15142 600/347 |
| 2017/0188912 A1* | 7/2017 | Halac | A61B 5/6848 |
| 2020/0077957 A1* | 3/2020 | Akiyama | A61B 5/6848 |

FOREIGN PATENT DOCUMENTS

| | | | | |
|---|---|---|---|---|
| JP | 2003-190282 A | 7/2003 | | |
| JP | 2004-136343 A | 5/2004 | | |
| JP | 2005-087613 A | 4/2005 | | |
| JP | 2007-167482 A | 7/2007 | | |
| JP | 4499128 B2 | 7/2010 | | |
| JP | 2011-104623 A | 6/2011 | | |
| JP | 2015-020706 A | 2/2015 | | |
| JP | 2016-059427 A | 4/2016 | | |
| WO | WO-9219150 A1 * | 11/1992 | ......... | A61B 5/14542 |
| WO | WO-2015/114706 A1 | 8/2015 | | |
| WO | WO-2016114398 A1 * | 7/2016 | ............. | A61M 1/14 |
| WO | WO-2016/191302 A1 | 12/2016 | | |

OTHER PUBLICATIONS

Machine Translation of Item N (WO 2016/114398) (Year: 2023).*
Machine Translation of JP 2001-321439 (Year: 2023).*
International Search Report and Written Opinion issued in connection with PCT Application No. PCT/JP2018/018181, dated Jul. 10, 2018.
International Searching Authority, "International Search Report," issued in connection with International Patent Application No. PCT/JP2018/018181, dated Jul. 10, 2018.
International Searching Authority, "Written Opinion," issued in connection with International Patent Application No. PCT/JP2018/018181, dated Jul. 10, 2018.
Office Action issued in the corresponding Japanese patent application No. 2022-161737, dated Jul. 11, 2023.

* cited by examiner

SENSOR AND METHOD FOR MANUFACTURING SENSOR

CROSS-REFERENCE TO RELATED APPLICATIONS

This is a bypass continuation of PCT Application No. PCT/JP2018/018181, filed on May 10, 2018, which claims priority to Japanese Application No. 2017-132085, filed on Jul. 5, 2017. The contents of these applications are hereby incorporated by reference in their entireties.

BACKGROUND

The present disclosure relates to a sensor and a method for manufacturing the sensor.

BACKGROUND ART

Conventionally, a technique of inserting or implanting a sensor inside a body of a subject such as a patient and detecting a substance to be measured (for example, glucose, pH, a physiologically active substance, protein, or the like) in a blood or a body fluid of the subject by the sensor has been conducted.

Japanese Patent No. 4499128 discloses an electrochemical sensor that is inserted and implanted into a patient using an insertion device and an insertion gun. In addition, PCT Publication No. WO 2016/191302 discloses a needle that can deliver a sensor percutaneously and in which a slot is formed.

SUMMARY

When the sensor is implanted in a body of a subject and performs detection of a substance to be measured for a predetermined period, such as one week, a needle member may be used only at the time of inserting a detection member, or the needle member and the detection member may be used while implanted in the body together. In either case, it is preferable that the needle member have sufficient strength, such that no impact occurs at the time of insertion and no bending or breakage occurs during the predetermined period in a daily life. In addition, it is preferable that the needle member have a configuration in which the stress to the subject is reduced.

An object of certain embodiments of the present disclosure is to provide a sensor including a needle member having a configuration capable of achieving both securement of strength and a reduction in diameter, and a method for manufacturing the sensor.

According to a first embodiment of the present disclosure, a sensor includes: a tubular needle member that defines a hollow portion; and a linear detection member located in the hollow portion. A thick portion protruding toward the hollow portion is provided on a side wall of the needle member.

According to one aspect, a receiving surface that receives the detection member is provided on a thick portion inner wall, formed by the thick portion, of an inner wall of the needle member.

According to one aspect, the receiving surface has a receiving shape that is configured to be in surface-contact with and to receive a partial region of an outer shape of a cross section of the detection member.

According to one aspect, the detection member has a substantially circular outer shape in the cross section, and the receiving surface is configured using a concave curved surface that receives the detection member.

According to one aspect, at least the two detection members are provided in the hollow portion, and the thick portion inner wall is provided with at least the two receiving surfaces that receive the at least two detection members.

According to one aspect, the thick portion inner wall includes: a top portion; a first side portion that is continuous from the top portion to one side of the needle member in a circumferential direction and in which a wall thickness of the needle member gradually decreases from the top portion toward the one side of the needle member in the circumferential direction; and a second side portion that is continuous from the top portion to another side of the needle member in the circumferential direction and in which the wall thickness of the needle member gradually decreases from the top portion toward the other side of the needle member in the circumferential direction, and the receiving surface is formed on at least one of the first side portion and the second side portion.

According to one aspect, an opening portion configured using a through-hole or a slit is formed on the side wall of the needle member.

According to one aspect, an opening reinforcement portion is provided in an edge portion of the side wall that defines the opening portion.

According to one aspect, the opening portion opposes the thick portion in a radial direction of the needle member.

According to one aspect, a blade surface portion including a blade surface inclined with respect to an axial direction of a central axis of the needle member and a needle tip, which is a distal end of the blade surface, is formed in a distal end portion of the needle member, the thick portion extends to a distal end opening of the needle member defined by the blade surface portion in the axial direction, and the thick portion is formed at a position where a line segment connecting the central axis of the needle member and the needle tip intersects the side wall in a plan view where the needle member is viewed from a distal end side.

According to another embodiment of the present disclosure, a method for manufacturing a sensor includes: a thickness pressing step of pressing a plate material to form a plate-shaped body having a thick portion; and a tubular shape pressing step of pressing the plate-shaped body into a tubular shape to form a tubular body.

According to one aspect, a linear detection member is enclosed in the plate-shaped body that is deformed into the tubular shape in the tubular shape pressing step.

According to one aspect, the method further includes a concave portion formation step of forming concave portions at outer edges of the plate material or the plate-shaped body that are aligned when being deformed into the tubular shape in the tubular shape pressing step.

According to one aspect, in the concave portion formation step, the concave portion is formed by bending a part of the outer edge of the plate material or the plate-shaped body.

According to another embodiment of the present disclosure, a method for manufacturing a sensor includes: a thickness pressing step of pressing a rod material to form a semi-tubular body having a thick portion and an open portion; and a tubular shape pressing step of pressing the semi-tubular body to be deformed into a tubular shape to form a tubular body.

According to one aspect, a linear detection member is enclosed in the semi-tubular body through the open portion in the tubular shape pressing step.

Advantageous Effects of Invention

According to certain embodiments of the present disclosure, it is possible to provide a sensor including a needle member having a configuration capable of achieving both adequate strength and reduced diameter, and a method for manufacturing the sensor.

DETAILED DESCRIPTION

Figure 1:
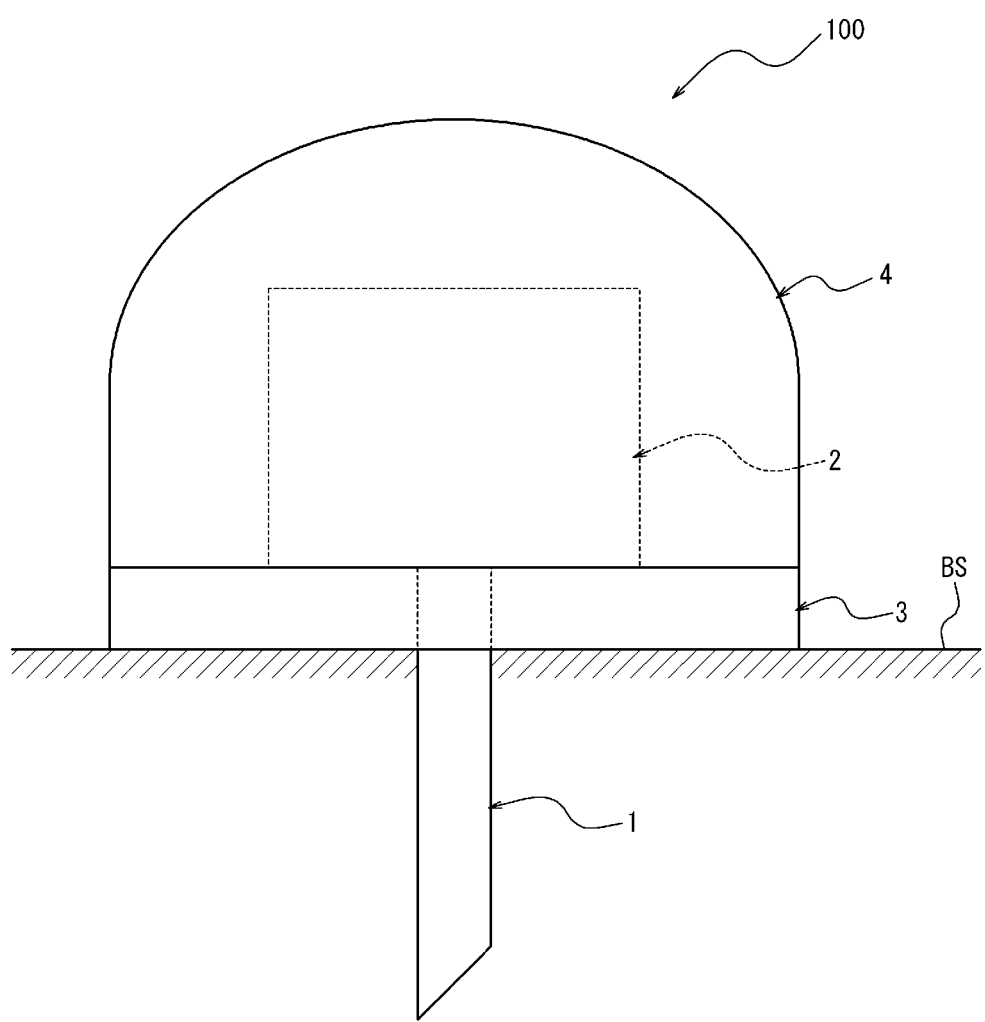
FIG. 1 is a view illustrating a measurement device provided with a sensor according to an embodiment of the present invention.

Hereinafter, embodiments of a sensor and a method for manufacturing the sensor according to the present invention will be described with reference to FIGS. 1 to 17. The same reference numerals are used for members and parts that are common among the drawings.

FIG. 1 is a view illustrating a measurement device 100 provided with a sensor 1 according to one embodiment of the present invention. As illustrated in FIG. 1, the measurement device 100 includes the sensor 1, a control unit 2, a support member 3, and a housing 4.

The sensor 1 detects a substance to be measured (analyte), and transmits information regarding a detection result to the control unit 2. The control unit 2 is constituted by a processor, a memory, a battery, and the like. The control unit 2 analyzes a detection signal received from the sensor 1 and transmits an analysis result to an external device such as a display device as necessary. The support member 3 supports the sensor 1. Specifically, the support member 3 supports the sensor 1 by holding a proximal end portion of a needle member 10, which will be described later, of the sensor 1. The housing 4 accommodates the control unit 2 therein, and is attached to the support member 3 in the state of covering the control unit 2.

The measurement device 100 is attached to a subject in a state where the sensor 1 has been inserted into a body. FIG. 1 illustrates a state where the control unit 2, the support member 3, and the housing 4 of the measurement device 100 are mounted on a body surface BS of the subject. The measurement device 100 measures the substance to be measured in a body fluid of the subject over time while being mounted on the subject. A period during which the measurement device 100 is mounted on the subject is appropriately defined by the determination of a doctor or the like to be several hours, several days, one week, one month, or the like.

The substance to be measured is not particularly limited; glucose, oxygen, pH, lactic acid, and the like in an interstitial fluid can be measured by selecting a detection member of the sensor.

In addition, the measurement device 100 illustrated in FIG. 1 may be configured to include an insertion mechanism that inserts the sensor 1 into the body. Alternatively, the insertion mechanism may be provided separately from the measurement device 100. In this case, the insertion mechanism may be configured to be detached from the measurement device 100 after the sensor 1 is inserted into the body.

Figure 2A:
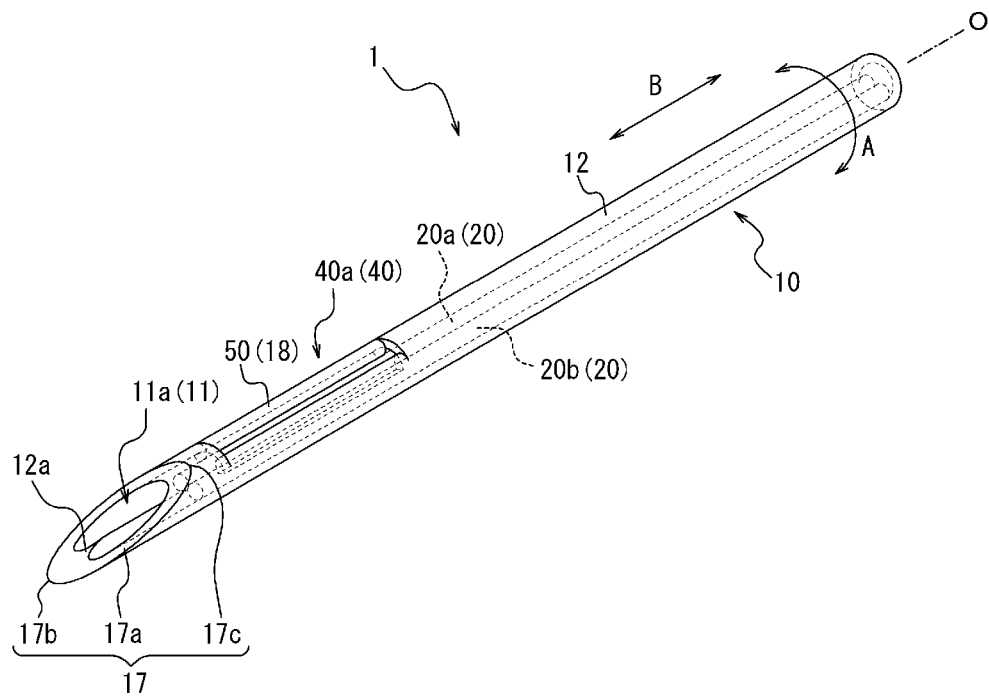
FIG. 2A is a perspective view illustrating the entire sensor alone illustrated in FIG. 1.
Figure 2B:
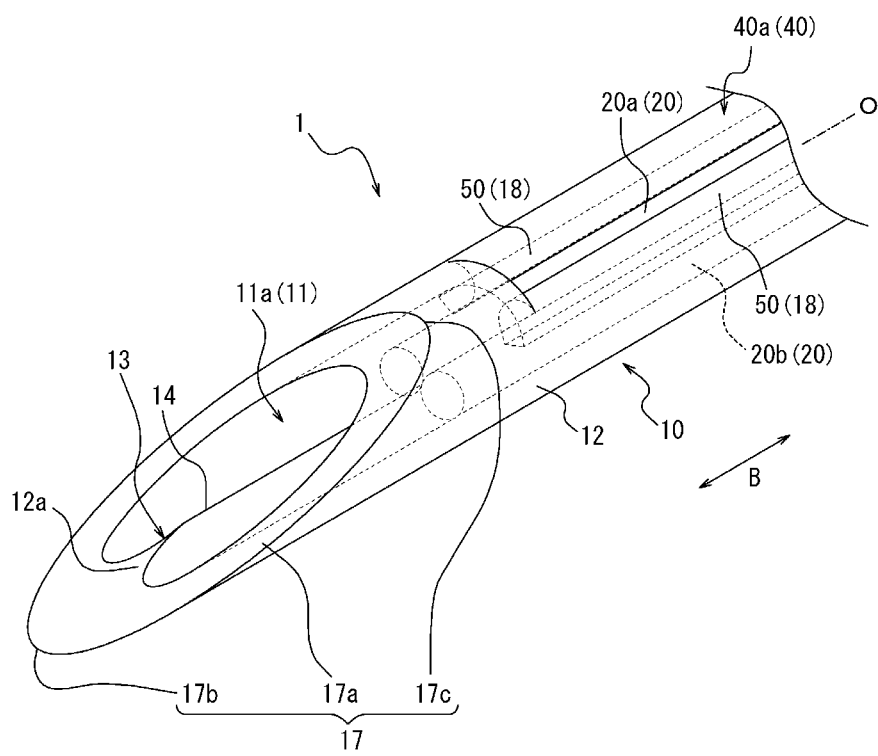
FIG. 2B is an enlarged perspective view illustrating a portion on a distal end side of the sensor illustrated in FIG. 2A.
Figure 3:
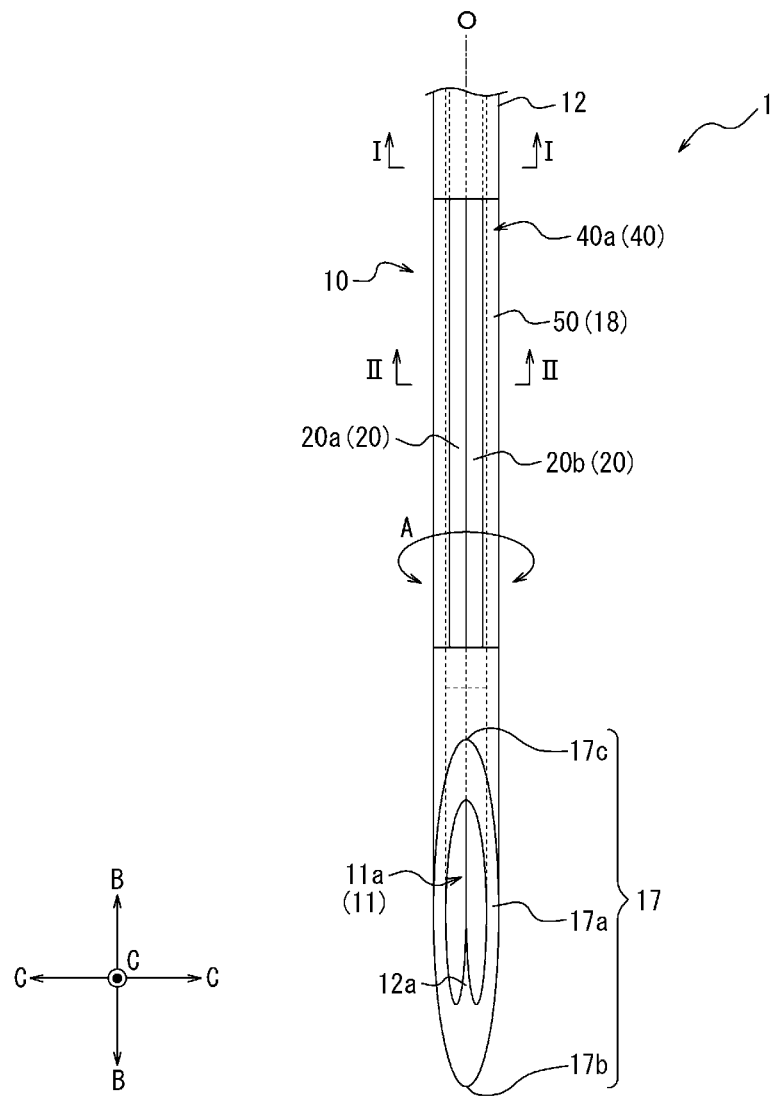
FIG. 3 is a front view of the portion on the distal end side of the sensor illustrated in FIG. 1.
Figure 4:
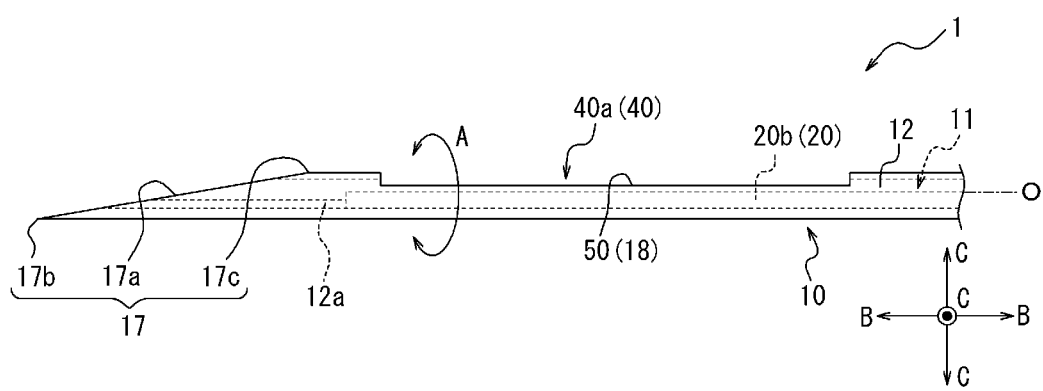
FIG. 4 is a side view of the portion on the distal end side of the sensor illustrated in FIG. 1.
Figure 5:
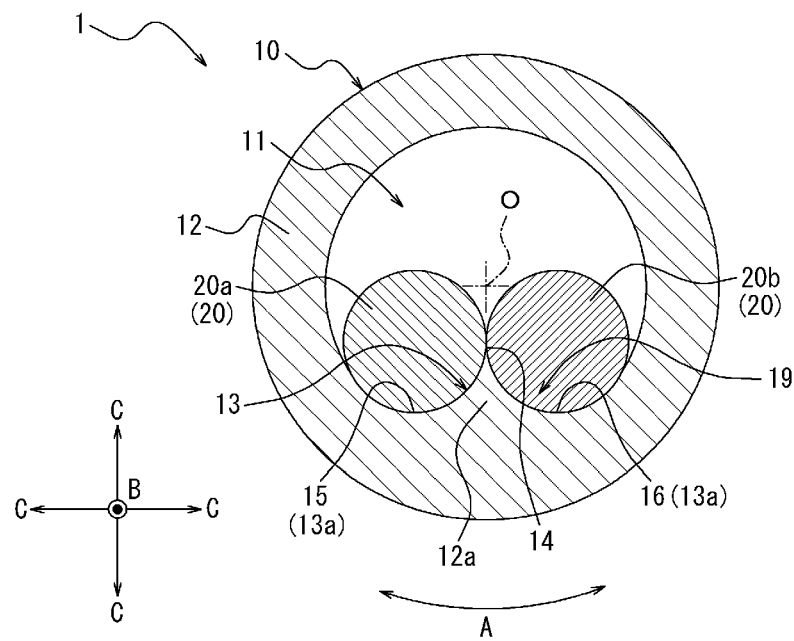
FIG. 5 is a cross-sectional view taken along line I-I in FIG. 3.
Figure 6:
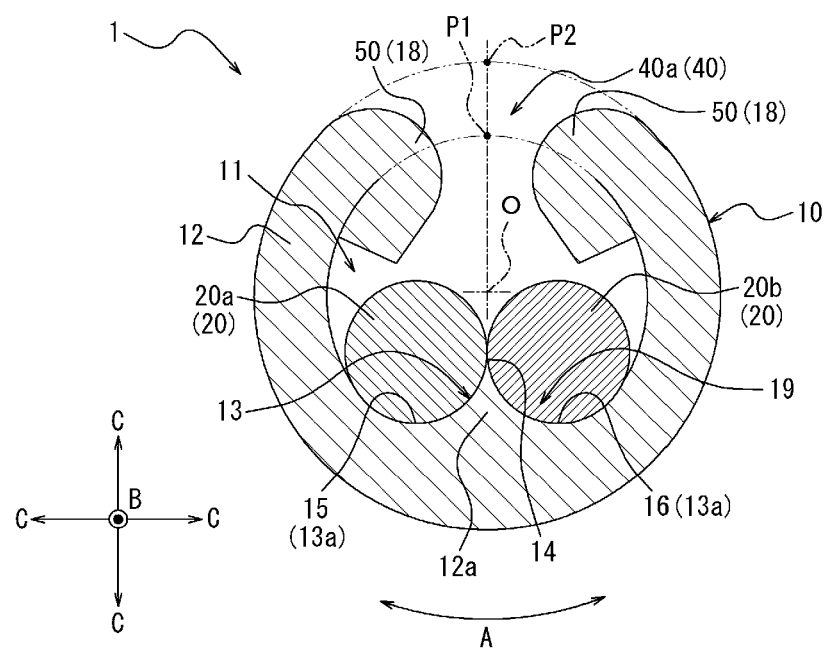
FIG. 6 is a cross-sectional view taken along line II-II in FIG. 3.

Hereinafter, the sensor 1 of the present embodiment will be described. FIGS. 2A and 2B are perspective views illustrating the sensor 1. Specifically, FIG. 2A is a perspective view illustrating the entire sensor 1, and FIG. 2B is an enlarged perspective view illustrating a portion on a distal end side of the sensor 1 illustrated in FIG. 2A. FIG. 3 is a front view of the portion on the distal end side of the sensor 1. FIG. 4 is a side view of the portion on the distal end side of the sensor 1. FIG. 5 is a cross-sectional view taken along line I-I in FIG. 3. FIG. 6 is a cross-sectional view taken along line II-II in FIG. 3.

As illustrated in FIGS. 2 to 6, the sensor 1 includes a needle member 10 and a detection member 20.

The needle member 10 is a tubular hollow needle that defines a hollow portion 11 therein. A thickness of the needle member 10 is, for example, 25 to 33 gauge (an outer diameter of 0.5 mm to 0.2 mm), and a length thereof is 1 mm to 10 mm, and preferably 3 to 6 mm. In addition, a wall thickness of the needle member 10 is set, for example, in the range of 0.02 mm to 0.15 mm at a position excluding a thick portion 12a to be described later.

As a material of the needle member 10, for example, a metal material, such as stainless steel, aluminum, an aluminum alloy, titanium, and a titanium alloy can be used. In the case of stainless steel, stainless steel conforming to SUS304, SUS304L, SUS321, and ISO 9626: 2016 defined in JIS G 4305: 2012 is preferable.

The thick portion 12a protruding toward the hollow portion 11 is provided on a side wall 12 of the needle member 10. Because the thick portion 12a is provided on the side wall 12 of the needle member 10 in this manner, it is possible to achieve both securement of strength of the needle member 10 and a reduction in diameter.

The thick portion 12a protrudes toward the hollow portion 11. In addition, the thick portion 12a is provided at a part of the side wall 12 of the needle member 10 in a circumferential direction A and extends along an axial direction B of a central axis O of the needle member 10. More specifically, the thick portion 12a of the present embodiment is provided at a part of the side wall 12 of the needle member 10 in the circumferential direction A along the axial direction B of the central axis O of the needle member 10. In addition, the side wall 12 of the needle member 10 of the present embodiment has a substantially uniform wall thickness at positions other than the thick portion 12a and an opening reinforcement portion 50 to be described later.

In other words, the thick portion 12a protrudes from an inner wall of the side wall 12 of the needle member 10, and thus, the inner wall has a surface that is not a circumferential surface in a cross-sectional view orthogonal to the central axis O of the needle member 10. On the other hand, an outer wall shape of the side wall 12 of the needle member 10 of the present embodiment has a circumferential surface or a substantially circumferential surface in a cross-sectional view orthogonal to the central axis O of the needle member 10 except for the position where the opening portion 40 to be described later is formed. Because the portion protruding to the outer side in the radial direction C of the needle member 10 is not formed on the outer wall of the side wall 12 of the needle member 10 of the present embodiment in this manner, it is possible to reduce a penetration resistance at the time of insertion into and/or removal from the body.

The above-described "circumferential direction A of the side wall 12 of the needle member 10" means a direction along the outer wall in a cross-sectional view of the needle member 10. In addition, the "the central axis O of the needle member 10" of the present embodiment means a central axis specified by only the portion where the outer wall has the circumferential surface in the cross-sectional view of the needle member 10. The "axial direction B" in the present embodiment substantially coincides with an extending direction of the needle member 10. Further, the "radial direction C of the needle member 10" in the present embodiment means a direction that extends in a radial shape about the central axis O of the needle member 10. Therefore, an inner side in the radial direction C of the needle member 10 means the central axis O side in the direction extending in the radial shape about the central axis O of the needle member 10. The outer side in the radial direction C of the needle member 10 means a side opposite to the central axis O side in the direction extending in the radial shape about the central axis O of the needle member 10.

In addition, a receiving surface 13a receiving the detection member 20 is provided on the thick portion inner wall 13, which is formed of the thick portion 12a, of the inner wall of the needle member 10. Because the receiving surface 13a is provided on the thick portion inner wall 13, it is possible not only to achieve both the securement of strength of the needle member 10 and the reduction in diameter using the thick portion 12a as described above but also to enhance position fixability in the hollow portion 11 of the linear detection member 20 to be described later. Because the position fixability is enhanced, it is possible to reduce noise caused by movement of the detection member 20 inside the needle member 10.

Further, the receiving surface 13a may have a receiving shape configured to be in surface-contact with and to receive a partial region of an outer shape of a cross section of the detection member 20. Because the receiving surface 13a is set to such a shape, it is possible to further enhance the position fixability in the hollow portion 11 of the linear detection member 20 to be described later. The detection member 20 of the present embodiment has a substantially circular outer shape in a cross section as will be described later. Thus, the receiving surface 13a of the present embodiment is formed of a concave curved surface that receives the detection member 20.

In addition, the two receiving surfaces 13a are provided in the thick portion inner wall 13 of the present embodiment, and the two receiving surfaces 13a receives the separate detection members 20, respectively.

More specifically, the thick portion inner wall 13 of the present embodiment has: a top portion 14; a first side portion 15 that is an inner wall, continuous from the top portion 14 to one side of the needle member 10 in the circumferential direction A, at a position where the wall thickness of the needle member 10 gradually decreases from the top portion 14 toward the one side in the circumferential direction A of the needle member 10; and a second side portion 16 that is an inner wall, continuous from the top portion 14 to the other side of the needle member 10 in the circumferential direction A, at a position where the wall thickness of the needle member 10 gradually decreases from the top portion 14 toward the other side of the needle member 10 in the circumferential direction A. Further, the receiving surfaces 13a are formed in the first side portion 15 and the second side portion 16, respectively. More specifically, the respective detection members 20 of the present embodiment are accommodated in receiving grooves 19 including the receiving surfaces 13a formed in the first side portion 15 and the second side portion 16, respectively.

Although the number of the receiving surfaces 13a provided on the thick portion inner wall 13 in the present embodiment is two in accordance with the number of the detection members 20 arranged in the hollow portion 11, the number is not limited thereto. The number of the receiving surfaces 13a is preferably two or three, but can be appropriately changed in accordance with an increase or a decrease of the number of the detection members 20 arranged in the hollow portion 11. In addition, the receiving surfaces 13a provided in the thick portion inner wall 13 of the present embodiment are formed respectively in the first side portion 15 and the second side portion 16, but may form only in any one thereof. However, it is preferable to form the receiving surfaces 13a, which receive the separate detection members 20, respectively in the first side portion 15 and the second side portion 16 as in the present embodiment in order to enhance the position fixability of each of the plurality of detection members 20. Further, even when it is preferable to arrange the detection members 20 to be separated from each other with the thick portion 12a interposed therebetween, the receiving surfaces 13a are formed in the first side portion 15 and the second side portion 16, respectively, as in the present embodiment. In such a case, the thick portion 12a is interposed between the adjacent detection members 20 such that the detection members 20 do not come into contact with each other.

In addition, the top portion 14 of the present embodiment is formed of a ridge line where the two receiving surfaces 13a intersect each other. With such a top portion 14, the two receiving surfaces 13a formed in the first side portion 15 and the second side portion 16 can be arranged closer to each other as compared to a case where the top portion is formed of a flat surface or a curved surface. As a result, it is easy to realize the configuration of the needle member 10 to improve the position fixability of the detection member 20 compactly without increasing the diameter of the needle member 10.

Further, a through-hole 40a, which serves as an opening portion 40 capable of introducing a body fluid, such as an interstitial fluid, of the subject into the hollow portion 11, is formed in the side wall 12 of the needle member 10 of the present embodiment. The hollow portion 11 communicates with the outside of the needle member 10 through the through-hole 40a and a distal end opening 11a. Thus, the body fluid of the subject easily flows in and out of the needle member 10, and the body fluid in contact with the detection member 20 located inside the needle member 10 is also easily replaced, as compared to the configuration without the opening portion 40. That is, it is possible to more accurately measure a temporal change of the substance to be measured.

As illustrated in FIG. 6, the through-hole 40a serving as the opening portion 40 opposes the thick portion 12a in the radial direction C of the needle member 10. That is, the thick portion 12a is provided at a position opposing the opening portion 40. By providing the thick portion 12a at such a position, the strength of the needle member 10 can be reinforced at a position of the opening portion 40 in the axial direction B regardless of a shape of the opening portion 40 even in the configuration in which the opening portion 40 is formed. That is, the desired opening portion 40 can be realized while suppressing a decrease in strength of the needle member 10. The thick portion 12a is preferably provided at least partially in the axial direction B of the needle member 10. It is more preferable to provide the thick portion 12a over the entire region in the axial direction B of the needle member 10 as in the present embodiment. In this manner, the strength of the needle member 10 can be enhanced in the entire region in the axial direction B of the needle member 10 as well as at the position of the opening portion 40 in the axial direction B of the needle member 10. As illustrated in FIG. 6, a gap is secured between the opening portion 40 and the detection member 20 in the hollow portion 11. In addition, the gap communicates in the axial direction B in the hollow portion 11 as illustrated in FIG. 5. That is, the body fluid that has flown into the hollow portion 11 from the opening portion 40 can move in the axial direction B through the above gap. As a result, it is easy to fill the periphery of the detection member 20 located in the hollow portion 11 with the body fluid, and it is possible to promote the detection of the substance to be measured by the detection member 20.

As illustrated in FIG. 6, the opening reinforcement portion 50 formed to be bent toward the hollow portion 11 is provided at an edge portion 18 of the side wall 12 that defines the through-hole 40a as the opening portion 40. Specifically, the opening reinforcement portions 50 of the present embodiment are respectively formed at the edge portions 18 on both sides in the circumferential direction A with respect to the through-hole 40a as the opening portion 40. More specifically, the side wall 12 of the present embodiment is formed using a plate material, and this plate material is bent toward the hollow portion 11 at positions on both the sides of the through-hole 40a in the circumferential direction A. In other words, the plate material constituting the side wall 12 of the present embodiment is folded back to be superimposed at the positions on both the sides of the through-hole 40a in the circumferential direction A, and the opening reinforcement portion 50 is formed of such a bent and stacked portion that has been folded and stacked. That is, the edge portion 18 defining the through-hole 40a is made thicker than the periphery in the circumferential direction A by the bent and stacked portion, and as a result, it is possible to enhance the strength of the edge portion 18 of the through-hole 40a as the opening portion 40.

As illustrated in FIGS. 2 to 6, the opening portion 40 of the present embodiment is the through-hole 40a, but the opening portion 40 can be configured using a slit extending to the distal end of the needle member 10 in the axial direction B of the needle member 10. In addition, the same opening reinforcement portion 50 as described above can be formed even in the case where the opening portion 40 is configured using the slit. A configuration in which the opening portion 40 is configured using the slit will be described later (see FIGS. 12 and 17). Here, the term "tubular shape" in the present embodiment includes a true circular shape or an elliptical shape. In addition, the term "tubular shape" in the present embodiment is not limited to an closed complete ring configuration but also a shape that does not form a closed complete ring due to presence of a gap such as a slit extending over the entire region in the extending direction of the needle member (the same direction as the axial direction B in the present embodiment), such as, for example, a C-shaped cross-sectional shape. When the opening portion 40 is provided to the distal end opening 11a, it is possible to remove the needle member 10 without passing through a connection point between the detection member 20 and the control unit 2 after inserting the detection member 20 into the body of the subject. That is, the needle member 10 can be used as an insertion needle that inserts only the detection member 20 into the living body.

Further, a blade surface portion 17 is formed at the distal end portion of the needle member 10 of the present embodiment. The blade surface portion 17 includes a blade surface 17a inclined with respect to the axial direction B of the central axis O of the needle member 10 and a needle tip 17b that is a distal end of the blade surface 17a. In addition, the blade surface portion 17 defines the distal end opening 11a that is one end of the hollow portion 11 of the needle member 10.

Here, the thick portion 12a of the present embodiment extends to the distal end opening 11a in the axial direction B of the needle member 10. Further, the thick portion 12a of the present embodiment is formed at a position where a line segment connecting the central axis O of the needle member 10 and the needle tip 17b intersects the side wall 12 in a plan view where the needle member 10 is viewed from the distal end side. More specifically, the thick portion 12a of the present embodiment is formed such that the top portion 14 is located on the line segment connecting the central axis O of the needle member 10 and the needle tip 17b in the plan view where the needle member 10 is viewed from the distal end side. In addition, the thick portion 12a in the distal end opening 11a does not protrude from the distal end opening 11a. Thus, it is possible to prevent the thick portion 12a from being caught on a skin of the subject at the time of insertion of the needle member 10 and to mitigate pain of the subject at the time of insertion as the thick portion 12a is provided in the vicinity of the needle tip 17b in the circumferential direction A of the needle member 10 as compared to the configuration in which the thick portion 12a is provided in the vicinity of a heel portion 17c of the blade surface portion 17 in the circumferential direction A. The heel portion 17c means a portion of the blade surface portion 17 that is continuous with an outer circumferential surface of the needle member 10 at the proximal end in the axial direction B.

In other words, the through-hole 40a as the opening portion 40 is formed at a position closer to the heel portion 17c than the needle tip 17b in the circumferential direction A as illustrated in FIGS. 3 and 4. More specifically, when a center position of the through-hole 40a in the circumferential direction A of the present embodiment is projected in a plan view where the needle member 10 is viewed from the distal end side, the center position of the through-hole 40a in the circumferential direction A is located on a straight line extending to the outer side in the radial direction C through the heel portion 17c starting from the central axis O of the needle member 10 in the same plane view. In FIG. 6, the center position of the through-hole 40a in the circumferential direction A is indicated by "P1" for convenience of the description. In addition, a position of an intersection between a straight line that passes through the heel portion 17c of the needle member 10 and is parallel to the central axis O and a cross section illustrated in FIG. 6 is indicated by "P2" in FIG. 6. Hereinafter, "P2" in FIG. 6 will be simply described as the position P2 of the heel portion 17c for convenience of the description. A positional relationship among the center position P1 of the through-hole 40a in the circumferential direction A, the central axis O, and the position P2 of the heel portion 17c illustrated in FIG. 6 is the same as a positional relationship in the plane view where the needle member 10 is viewed from the distal end side. That is, when the center position P1 of the through-hole 40a in the circumferential direction A, the central axis O, and the position P2 of the heel portion 17c illustrated in FIG. 6 are projected in the plan view the needle member 10 is viewed from the distal end side, the center position P1 of the through-hole 40a in the circumferential direction A of the present embodiment is located on a straight line extending to the outer side in the radial direction C through the position P2 of the heel portion 17c starting from the central axis O of the needle member 10. However, the straight line passing through the central axis O and the position P2 of the heel portion 17c does not necessarily coincide with the straight line passing through the central axis O and the center position P1 in a cross-sectional view at the position of the opening portion 40 (see FIG. 6). Even in such a case, the straight line passing through the central axis O and the position P2 of the heel portion 17c preferably passes through the opening portion 40 in the cross-sectional view at the position of the opening portion 40 (see FIG. 6).

The detection member 20 is a linear member located in the hollow portion 11 of the needle member 10. As the detection member 20, a member that detects an electrical signal according to the amount or concentration of the substance to be measured can be used. The detection member 20 extends in the hollow portion 11 along the axial direction B of the needle member 10.

More specifically, the detection member 20 of the present embodiment is a wire electrode having a circular cross-sectional shape. As illustrated in FIGS. 2 to 6, the wire electrodes as the two detection members 20 are accommodated in the hollow portion 11 in the present embodiment. An outer diameter of the wire electrode as the detection member 20 of the present embodiment is 0.02 mm to 0.2 mm. Hereinafter, the two detection members 20 will be described as the "detection members 20" in the case of being described without being distinguished, and one of the two detection members 20 will be describes as a "first detection member 20a", and the other will be described as a "second detection member 20b" when the two detection members 20 are described in a distinguished manner.

The first detection member 20a includes a detection unit configured using a conductive core material as a base to detect the substance to be measured on an outer wall of the core material; and a protective portion obtained by coating the top of the outer wall of the core material with an insulating material. The detection unit is a working electrode that detects a change in electrical characteristics of the substance to be measured, and is formed on the surface of the core material using a thin film forming means such as dipping, electrolytic polymerization, and sputtering. In the present embodiment, the second detection member 20b constitutes a reference electrode with respect to the working electrode as the above-described detection unit. Three detection members 20 may be arranged in the hollow portion 11, and the working electrode, the reference electrode, and a counter electrode may be constituted by the three detection members 20, respectively. In addition, the needle member 10 may be used as the reference electrode or the counter electrode.

In addition, a connection portion that penetrates through the support member 3 and is connected to the control unit 2 is provided at a proximal end portion of the detection member 20 of the present embodiment. Information regarding the substance to be measured detected by the detection unit is transmitted to the control unit 2 via the connection portion.

Further, a fixing member that fixes the position of the detection member 20 with respect to the needle member 10 may be provided at the position of the proximal end portion of the needle member 10. The fixing member can be, for example, made of a fixing material such as an adhesive. If such a fixing member is used, the position of the detection member 20 with respect to the needle member 10 can be fixed at the proximal end portion of the needle member 10. Even when the fixing member is provided at the proximal end portion of the needle member 10, a portion of the detection member 20 located on the distal end side of the proximal end portion of the needle member 10 can move in the radial direction C of the needle member 10, but the needle member 10 of the present embodiment is provided with the above-described receiving surface 13a, and thus, it is also difficult to move the portion of the detection member 20 located on the distal end side of the needle member 10. The fixing member is not limited to the above-described example made of the fixing material such as the adhesive, and may be a fixing member, for example, configured using an elastic material such as rubber that is locked by the needle member 10 by being pinched and supported by the needle member 10.

Figure 7:
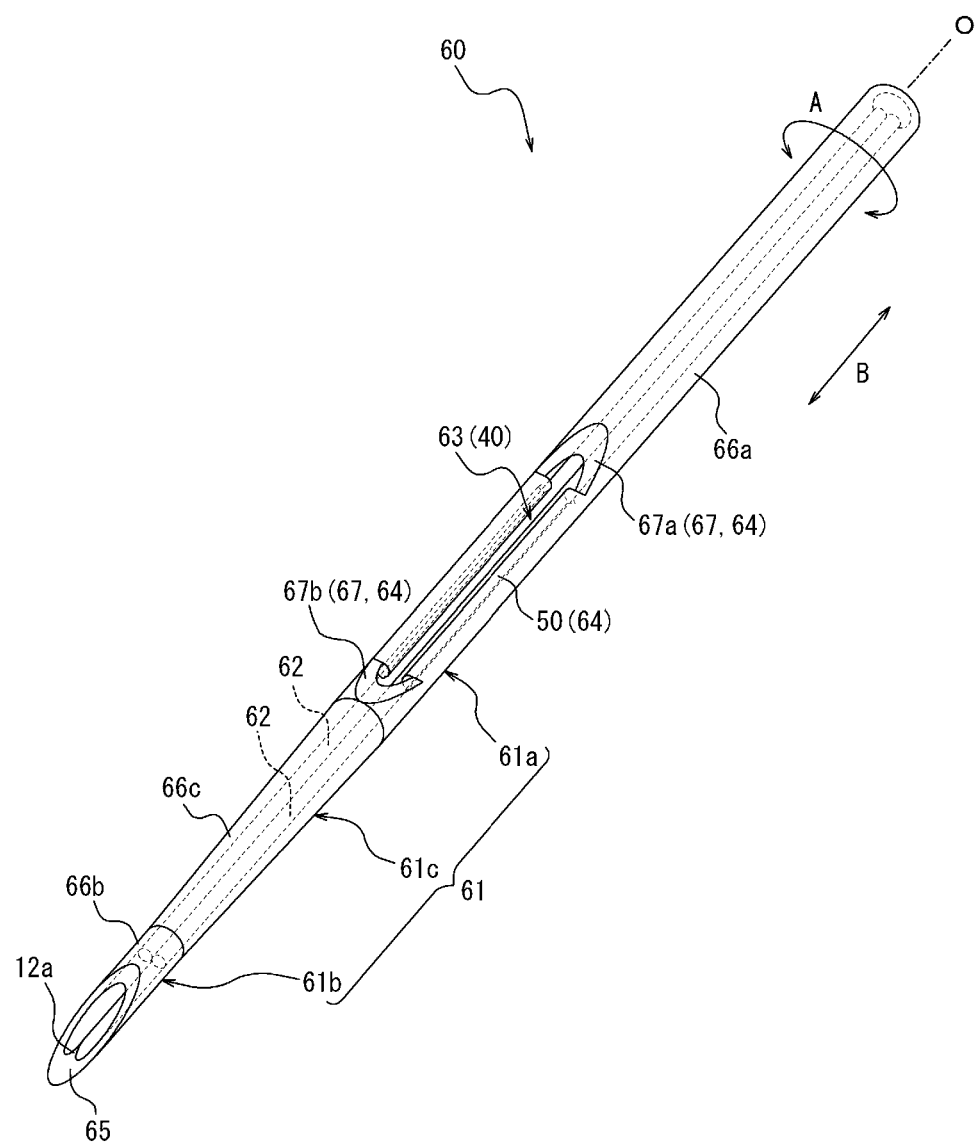
FIG. 7 is a perspective view illustrating a sensor according to an embodiment of the present invention.
Figure 8:
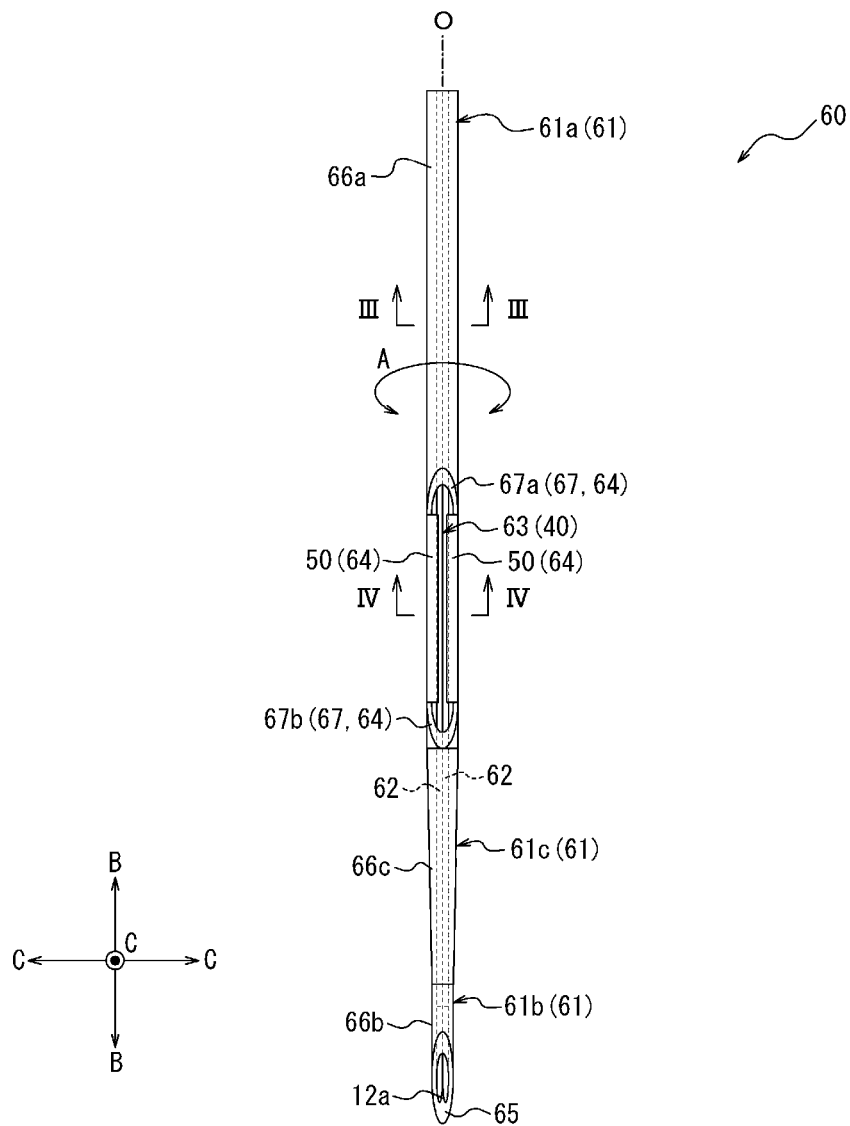
FIG. 8 is a front view of the sensor illustrated in FIG. 7.
Figure 9:
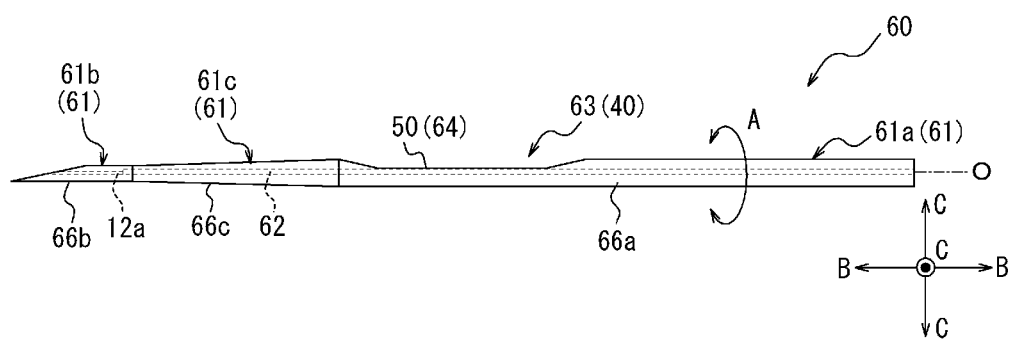
FIG. 9 is a side view of the sensor illustrated in FIG. 7.
Figure 10:
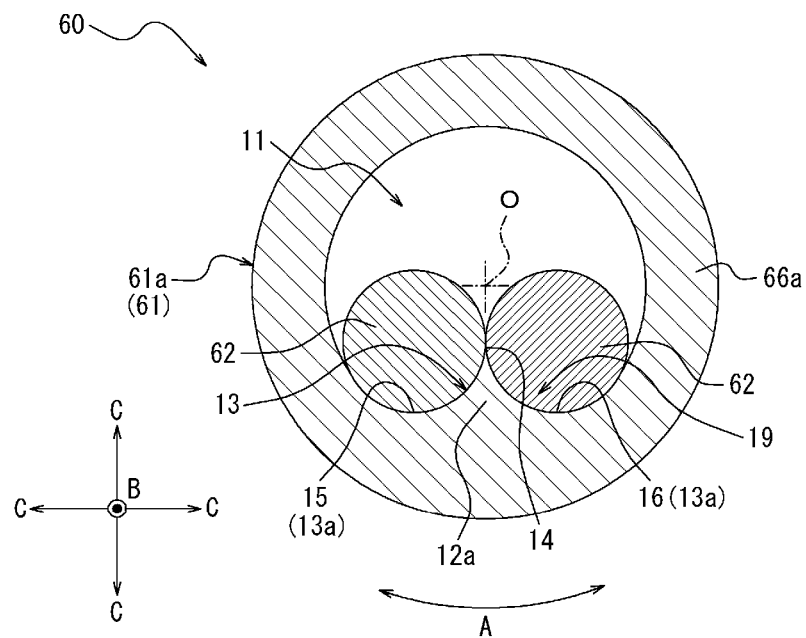
FIG. 10 is a cross-sectional view taken along line III-III in FIG. 8.
Figure 11:
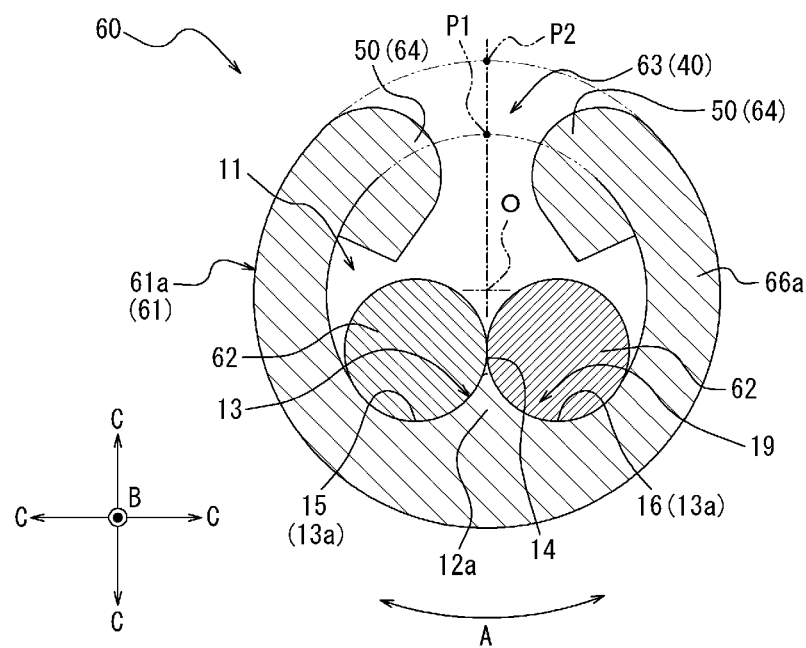
FIG. 11 is a cross-sectional view taken along line IV-IV in FIG. 8.

Next, a sensor 60 as an embodiment different from the above-described sensor 1 will be described. FIG. 7 is a perspective view of the sensor 60. FIG. 8 is a front view of the sensor 60. FIG. 9 is a side view of the sensor 60. FIG. 10 is a cross-sectional view taken along line III-III in FIG. 8, and FIG. 11 is a cross-sectional view taken along line IV-IV in FIG. 8.

As illustrated in FIGS. 7 to 11, the sensor 60 includes a needle member 61 and a detection member 62. The detection member 62 is the same as the detection member 20 of the sensor 1 described above, and thus, will not be described here.

The needle member 61 is different from the needle member 10 of the sensor 1 described above in terms that the needle member 61 has a shape having a different outer diameter depending on a position in the axial direction B of the central axis O. In addition, a through-hole 63 as the opening portion 40 is formed in the needle member 61 similarly to the needle member 10 of the sensor 1 described above, but is different from the needle member 10 of the sensor 1 described above in terms of a shape of an edge portion 64 defining the through-hole 63. Hereinafter, a difference of the needle member 10 in the needle member 61 will be mainly described, and the common configurations will not be described.

The needle member 61 includes: a body portion 61a; a distal end portion 61b that has a smaller outer diameter than the body portion 61a and in which the blade surface portion 65 is formed; and a tapered portion 61c that is located between the body portion 61a and the distal end portion 61b and whose outer diameter gradually decreases from the body portion 61a to the distal end portion 61b in the axial direction B.

The body portion 61a has substantially constant inner diameter and outer diameter regardless of the position in the axial direction B. A thickness of the body portion 61a in the present embodiment is 17 to 29 gauge, and preferably 29 gauge (having an outer diameter of about 0.3 mm). In addition, the through-hole 63 as the opening portion 40 described above is formed in a side wall 66a of the body portion 61a, and is not formed at the positions of the distal end portion 61b and the tapered portion 61c. That is, the through-hole 63 is formed only in the side wall 66a of the body portion 61a.

The distal end portion 61b has substantially constant inner diameter and outer diameter regardless of the position in the axial direction B. A thickness of the distal end portion 61b in the present embodiment is 21 gauge to 33 gauge, and preferably 33 gauge (having an outer diameter of about 0.2 mm). The blade surface portion 65 formed in a part including a distal end of the distal end portion 61b is the same as the blade surface portion 17 of the needle member 10 of the sensor 1 described above.

A proximal end side in the axial direction B of the side wall 66c of the tapered portion 61c is continuous with the side wall 66a of the body portion 61a, and a distal end side in the axial direction B of the side wall 66c of the tapered portion 61c is continuous with the side wall 66b of the distal end portion 61b. That is, a thickness of the proximal end of the side wall 66c of the tapered portion 61c in the axial direction B is 29 gauge similarly to the body portion 61a. In addition, a thickness of the distal end of the side wall 66c of the tapered portion 61c in the axial direction B is 33 gauge similarly to the distal end portion 61b.

Next, the edge portion 64 defining the through-hole 63 as the opening portion 40 will be described. The opening reinforcement portion 50 formed by folding a plate material is provided at portions, located on both sides in the circumferential direction A of the needle member 61, of the edge portion 64 of the through-hole 63 as the opening portion 40 illustrated in FIGS. 7 to 11, which is similar to the opening reinforcement portion 50 in the needle member 10 of the sensor 1. Meanwhile, the portions, located on both the sides in the axial direction B of the needle member 61, of the edge portion 64 of the through-hole 63 as the opening portion 40 illustrated in FIGS. 7 to 11 are configured using slope portions 67 that are inclined with respect to the axial direction B. Specifically, the edge portion 64 on the proximal end side in the axial direction B with respect to the through-hole 63 is configured using a first slope portion 67a that is inclined so as to approach to the central axis O as proceeding toward the distal end side in the axial direction B. In addition, the edge portion 64 on the distal end side in the axial direction B with respect to the through-hole 63 is configured using a second slope portion 67b that is inclined so as to be away from the central axis O as proceeding toward the distal end side in the axial direction B. Because the edge portions 64 on both the sides in the axial direction B of the through-hole 63 as the opening portion 40 are configured as the above-described slope portions 67 in this manner, it is possible to reduce a piercing resistance at the time of inserting or removing the needle member 61 into or from a subject as compared to the edge portion 18 that is constituted by the plane orthogonal to the central axis O at the same position of the sensor 1 described above. In particular, the first slope portion 67a and the second slope portion 67b contribute to the reduction of the piercing resistance both the insertion and the removal of the needle member 61. That is, the first slope portion 67a and the second slope portion 67b can reduce pain accompanying a change in diameter of the needle member 61 and hooking during the insertion and removal in a skin insertion site of the subject.

As illustrated in FIGS. 7 to 9, the second slope portion 67b reaches a position of a ridge line formed by an intersection between an outer circumferential surface of the body portion 61a and an outer circumferential surface of the tapered portion 61c. As a result, it is possible to suppress an increase of the piercing resistance caused by the ridge line formed by the intersection between the outer circumferential surface of the body portion 61a and the outer circumferential surface of the tapered portion 61c.

Figure 12:
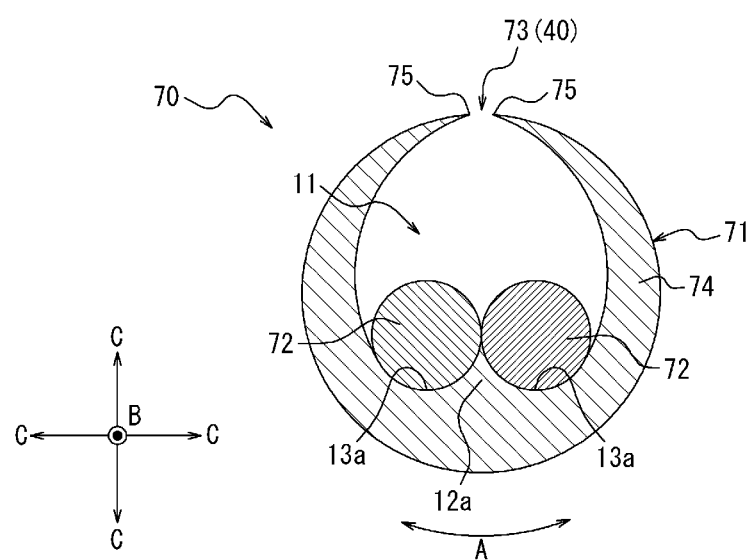
FIG. 12 is a cross-sectional view illustrating a sensor according to an embodiment of the present invention.

Next, a sensor 70 as an embodiment different from the above-described sensor 1 and sensor 60 will be described. FIG. 12 is a view illustrating a cross section of the sensor 70. The sensor 70 includes a needle member 71 and a detection member 72. The needle member 71 is different from the needle member 10 of the sensor 1 described above in terms that a slit 73 as the opening portion 40 is formed. The needle member 71 has a substantially C-shaped cross section, and the slit 73 extends over the entire region in the axial direction B of the needle member 71.

In addition, in a side wall 74 of the needle member 71 illustrated in FIG. 12 is different from the needle member 10 of the sensor 1 described above in terms that the opening reinforcement portion 50 is not provided in an edge portion 75 of the slit 73. And, a wall thickness of the side wall 74 of the needle member 71 gradually decreases from the thick portion 12a toward the edge portion 75 of the slit 73 in the circumferential direction A of the needle member 71 as illustrated in FIG. 12. As a result, it is possible to increase an internal volume of a hollow portion, and thus, it is possible to accommodate the detection member 72 without increasing a diameter of the sensor 70 even if a cross-sectional shape in a short-axis direction of the detection member 72 is flat or elliptical.

The other configurations of the needle member 71 are the same as those of the needle member 10 of the sensor 1 described above, and thus, will not be described here. In addition, the detection member 72 of the sensor 70 is also similar to the detection member 20 of the sensor 1 described above, and thus, will not be described here.

Figure 13:
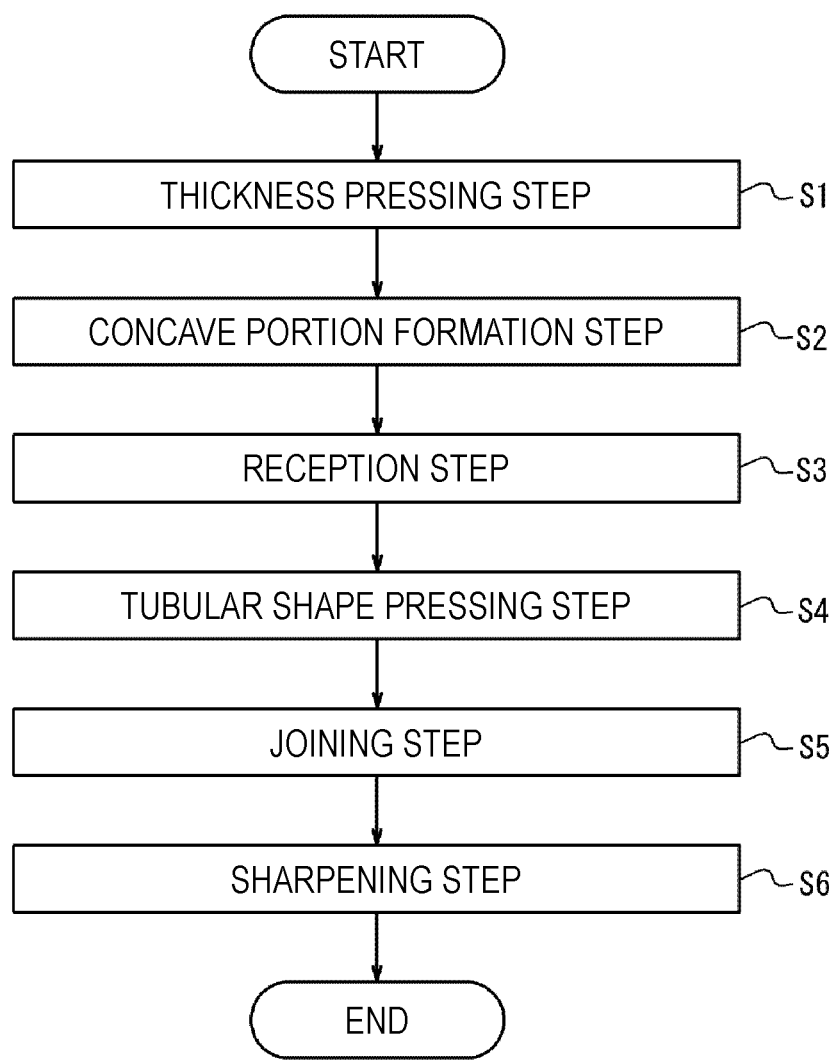
FIG. 13 is a view illustrating a method for manufacturing the sensor illustrated in FIG. 1.
Figure 14A:
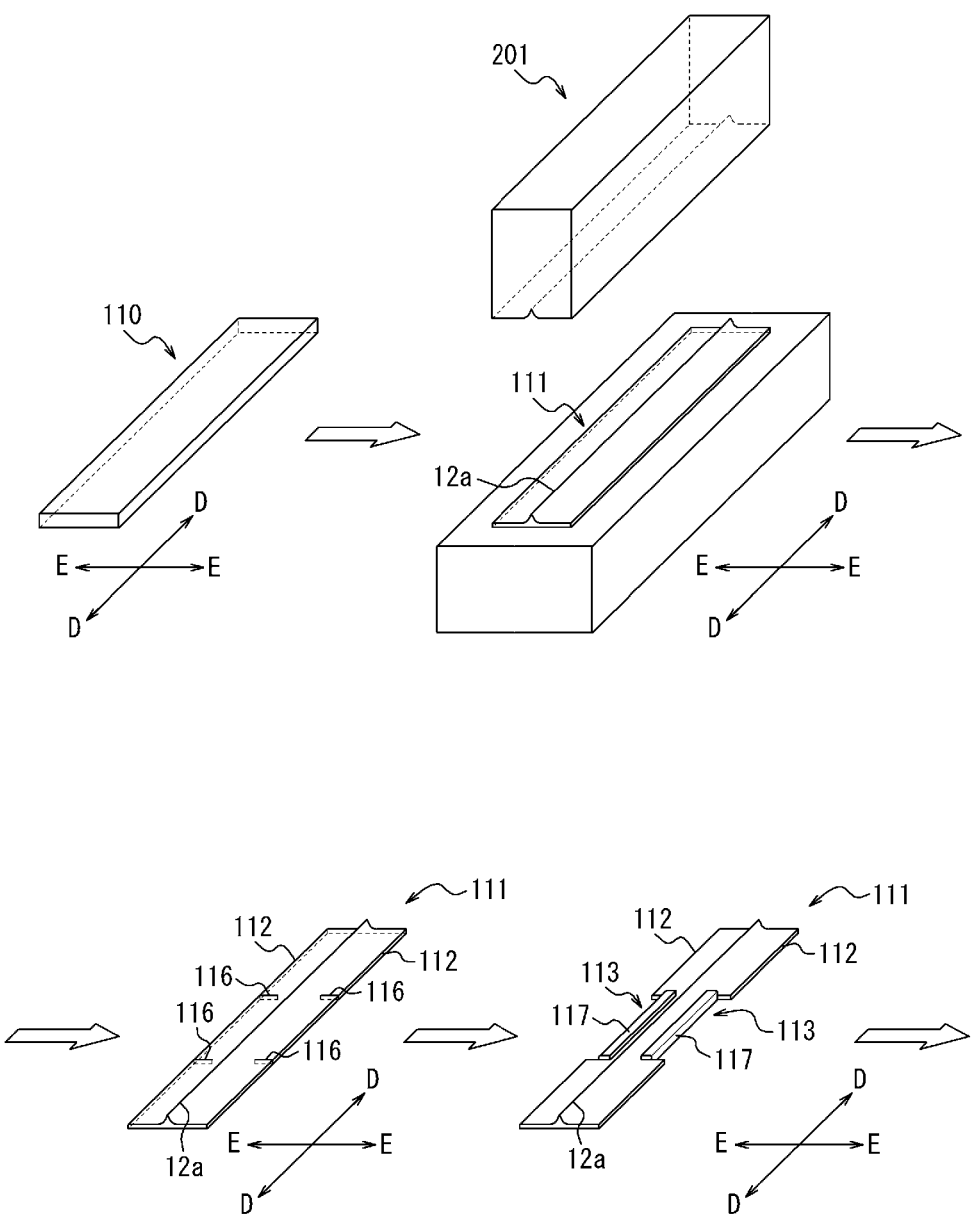
FIG. 14A is a schematic view illustrating an outline of a part of a series of steps illustrated in FIG. 13.
Figure 14B:
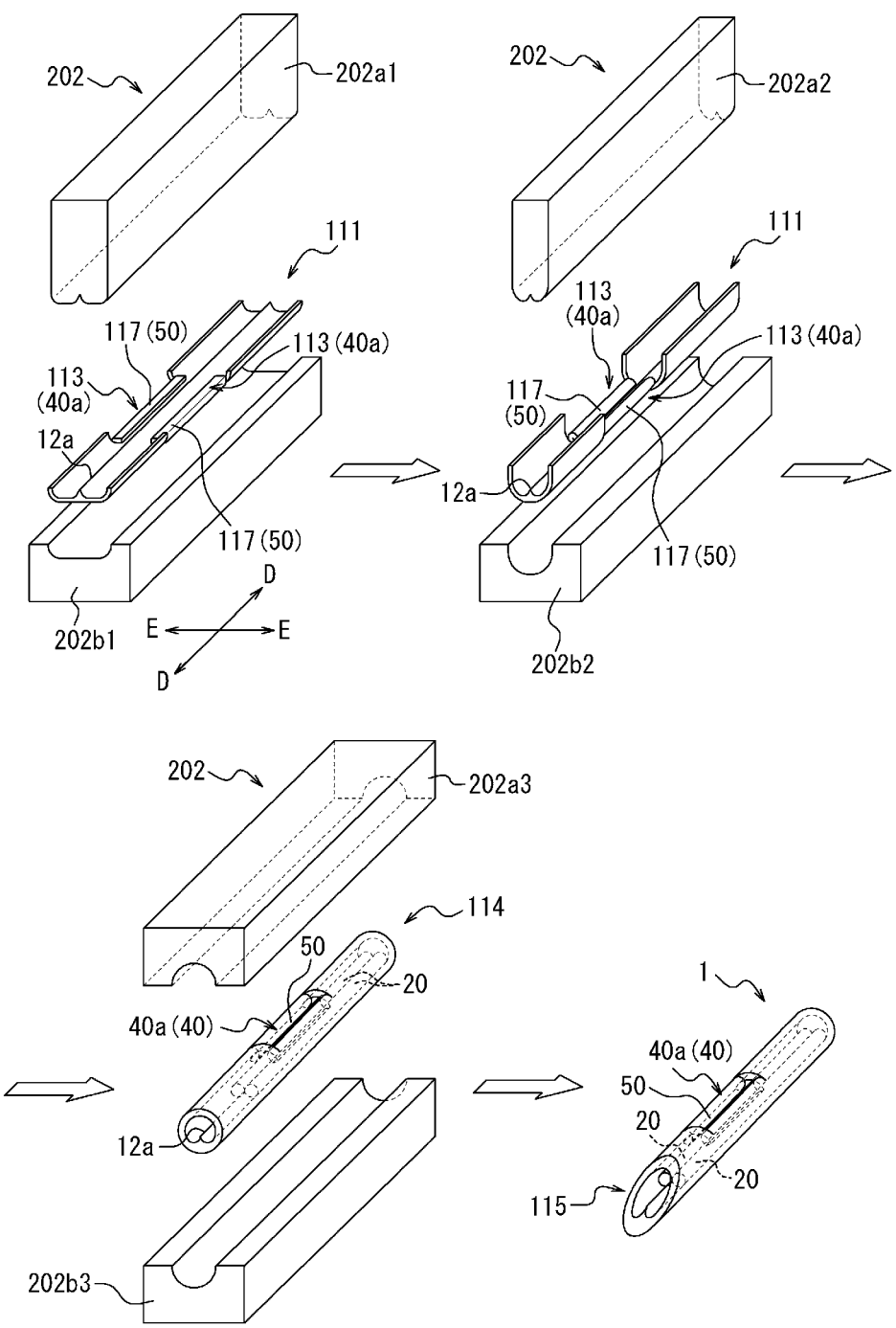
FIG. 14B is a schematic view illustrating an outline of a part of the series of steps illustrated in FIG. 13.
Figure 15:
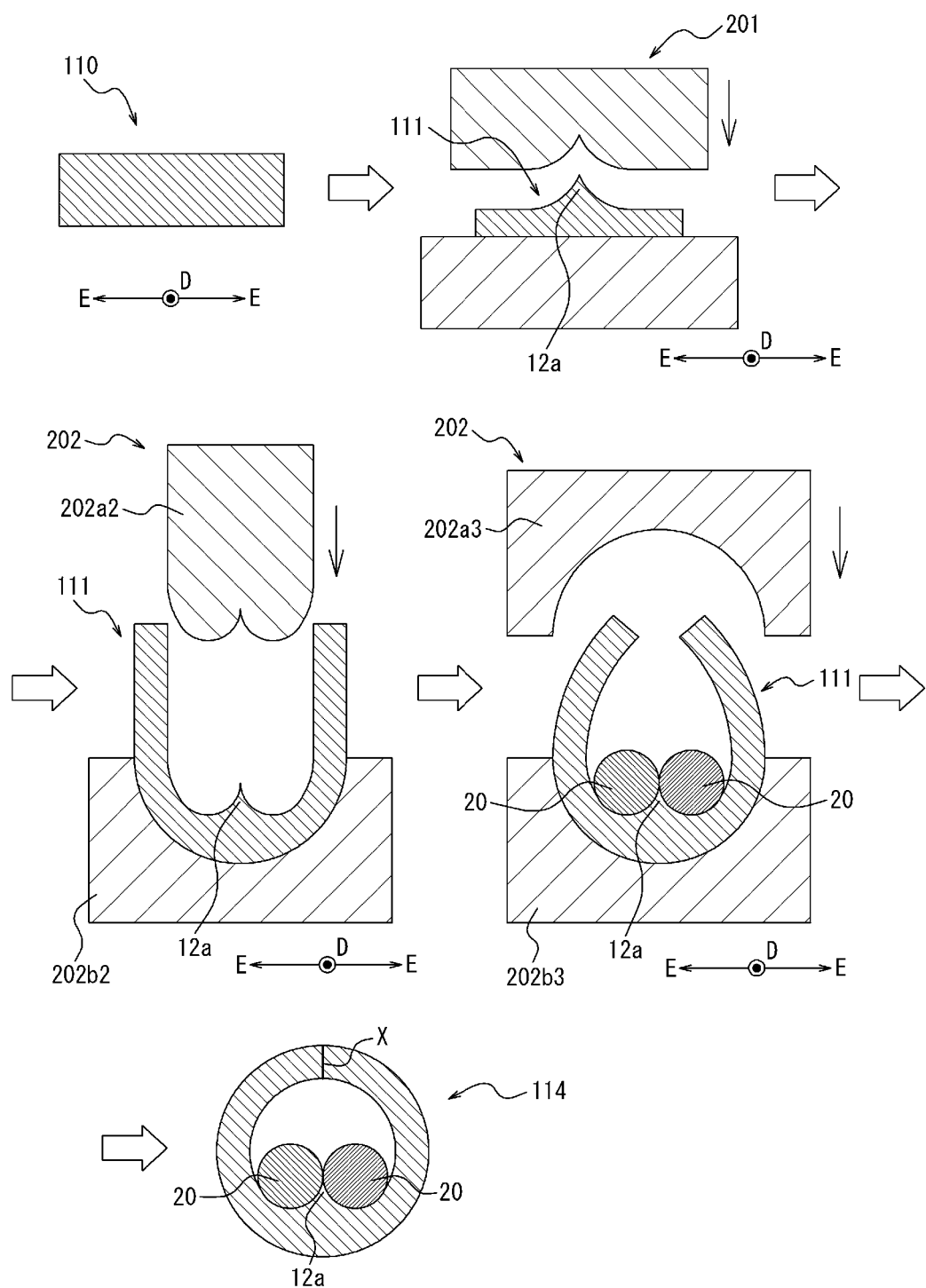
FIG. 15 is a view illustrating a temporal change of a cross-sectional shape of a material to be pressed that is subjected to pressing in the series of steps of FIG. 13.

Next, a method for manufacturing the sensor 1 will be described. FIG. 13 is a flowchart illustrating an example of a method for manufacturing the sensor 1, and FIGS. 14A and 14B are schematic views illustrating an outline of a series of steps illustrated in FIG. 13. The method for manufacturing the sensor 1 illustrated in FIGS. 13, 14A, and 14B includes: a thickness pressing step S1 of pressing a plate material 110 using a first press-molding machine 201 to form a plate-shaped body 111 having the thick portion 12a; a concave portion formation step S2 of forming a concave portion 113 at an outer edge 112 of the plate-shaped body 111; a reception step S3 of receiving the plate-shaped body 111 in which the concave portion 113 has been formed in a second press-molding machine 202; a tubular shape pressing step S4 of pressing the plate-shaped body 111 continuously using the second press-molding machine 202 to be deformed into a tubular shape to form a tubular body; a joining step S5 of welding or bonding a portion of a joint X of the plate-shaped body 111, which has been deformed into the tubular shape, to form a cylindrical body 114; and a sharpening step S6 of forming the blade surface portion 115 at one end portion of the cylindrical body 114. FIG. 15 is a view illustrating a temporal change of a cross-sectional shape of a material to be pressed that is subjected to pressing in the series of steps S1 to S6 of FIGS. 13, 14A, and 14B. The respective steps S1 to S6 in FIG. 13 will be described in detail with reference to FIGS. 14A, 14B, and 15. White arrow in FIGS. 14A, 14B, and 15 represent a temporal change in the steps. Specifically, an outline of the thickness pressing step S1 is illustrated in two drawings depicted on the upper part of FIG. 14A, and the drawing depicted on the uppermost part of FIG. 15. An outline of the concave portion formation step S2 is illustrated in the two drawings depicted in the lower part of FIG. 14A. Outlines of the reception step S3 and the tubular shape pressing step S4 are illustrated in two drawings depicted on the upper part of FIG. 14B, a drawing depicted on the left of the lower part of FIG. 14B, and two drawings depicted in the middle part of FIG. 15. An outline of the joining step S5 is illustrated in a drawing depicted on the left of the lower part of FIG. 14B and a drawing depicted in the lowermost part of FIG. 15. An outline of the sharpening step S6 is illustrated in a drawing depicted on the right of the lower part of FIG. 14B.

In the thickness pressing step S1, the plate material 110, which is made of metal and has a substantially uniform thickness, is pressed using the first press-molding machine 201 to form the plate-shaped body 111 that has the thick portion 12a as illustrated in FIGS. 14A and 15. The plate-shaped body 111 immediately after formation of the plate material 110 and the thick portion 12a illustrated in FIGS. 14A and 15 is the plate material 110 and the plate-shaped body 111 that have rectangular shapes. At this time, the thick portion 12a of the plate-shaped body 111 extends over the entire region in the longitudinal direction D of the plate-shaped body 111. In addition, the thick portion 12a protrudes from a periphery on a surface on one side in a thickness direction of the plate-shaped body 111, but forms the uniform surface with the periphery on a surface on the other side in the thickness direction of the plate-shaped body 111.

A plate thickness of the plate material 110 illustrated in FIGS. 14A and 15 is 0.15 mm. The plate material 110 is pressed to form the plate-shaped body 111 that has the thick portion 12a of which thickness is 0.15 mm and minimum thickness is 0.05 mm. However, the plate thickness of the plate material 110 and the thickness of each portion of the plate-shaped body 111 are not limited to the above-described thicknesses, and can be designed as appropriate in accordance with the thickness of the detection member of the sensor to be manufactured or the like.

The thick portion 12a illustrated in FIGS. 14A, 14B, and 15 is formed only at one point at a center in a lateral direction E of the plate-shaped body 111 (a center in a circumferential direction at a stage in the middle of being pressed into the tubular shape), but may be formed at a plurality of positions in the lateral direction E of the plate-shaped body 111.

In addition, the plate material 110 is pressed to form the plate-shaped body 111 having the thick portion 12a in the thickness pressing step S1 illustrated here, but a rod material may be pressed to form a plate-shaped body having a thick portion. A method for forming the thick portion by pressing the bar material will be described later (see FIG. 17).

As illustrated in FIG. 14A, in the concave portion formation step S2, a plurality of notches 116 corresponding to a width of the above-described opening reinforcement portion 50 (see FIG. 2A and the like) in the axial direction B (the same direction as the longitudinal direction D) are formed, respectively, at the linear outer edges 112 on both the sides in the lateral direction E of the plate-shaped body 111. Further, a portion between the adjacent notches 116 in each of the outer edges 112 is folded toward a side where the thick portion 12a is formed in the thickness direction of the plate-shaped body 111 to form a bending piece 117. The bending piece 117 is folded until coming into contact with a surface where the thick portion 12a of the plate-shaped body 111 is formed to cause a portion of the bending piece 117 of the plate-shaped body 111 to have a two-layered stacked structure, and to form the concave portion 113 in the outer edge 112. That is, the concave portion 113 is formed by bending a part of the outer edge 112 of the plate-shaped body 111 in the concave portion formation step S2 illustrated in FIG. 14A. The portion of the two-layered stacked structure formed by the bending piece 117 becomes the above-described opening reinforcement portion 50 at the time of completing the sensor 1. In addition, the concave portion 113 becomes the through-hole 40a as the opening portion 40 described above at the time of completing the sensor 1. In other words, the concave portion 113 to serve as the through-hole 40a can be formed at the same time as forming the bending piece 117 to serve as the opening reinforcement portion 50 by bending a part of the outer edge 112 of the plate-shaped body 111 in the concave portion formation step S2 illustrated in FIG. 14A.

Next, the plate-shaped body 111 in which the thick portion 12a and the concave portion 113 have been formed is installed in the second press-molding machine 202 in the reception step S3. Further, the plate-shaped body 111 is deformed into a tubular shape to form the tubular body in the tubular shape pressing step S4 as illustrated in FIGS. 14B and 15. The plate-shaped body 111 is subjected to pressing a plurality of times to be deformed into a tubular shape while being gradually curved by the second press-molding machine 202. FIGS. 14B and 15 illustrate a first upper die 202a1 and a first lower die 202b1 that curve only both end portions in the lateral direction E of the plate-shaped body 111, a second upper die 202a2 and a second lower die 202b2 that deform the plate-shaped body 111 into a tubular shape in the half in the lateral direction E, and a third upper die 202a3 and a third lower die 202b3 that deform the plate-shaped body 111 into a tubular shape. Here, additional upper and lower dies may be further used at a stage in the middle of deforming the plate-shaped body 111 into the tubular shape. The first upper die 202a1 and the second upper die 202a2 come into contact with the surface where the thick portion 12a of the plate-shaped body 111 is formed, and the third upper die 202a3 comes into contact with a surface opposite to the surface where the thick portion 12a of the plate-shaped body 111 is formed. In addition, the second lower die 202b2 and the third lower die 202b3 have the same shape in the present embodiment.

In the tubular shape pressing step S4, the linear detection member 20 can be enclosed in the plate-shaped body 111 deformed into the tubular shape. Specifically, in the tubular shape pressing step S4, when the plate-shaped body 111 is curved to some extent to reach a stage at which the upper die (for example, the third upper die 202a3) in contact with the surface opposite to the surface where the thick portion 12a of the plate-shaped body 111 is formed, the detection member 20 is installed inside the plate-shaped body 111 in the state of being curved to some extent before executing pressing with the upper die. Further, after installation of the detection member 20, the pressing is executed using the upper die in contact with the surface on the opposite side to the surface where the thick portion 12a of the plate-shaped body 111 is formed, that is, the surface to serve as the outer circumferential surface of the needle member 10 (see FIG. 2A and the like) of the completed sensor 1. In this manner, the plate-shaped body 111 can be deformed into a tubular shape so as to serve as an inner surface along an outer shape of the detection member 20. In this manner, the detection member 20 is arranged in advance at the stage in the middle of or before deforming the plate-shaped body 111 into the tubular shape, and the tubular shape pressing step S4 is completed in the state of enclosing the detection member 20. In this case, a step of accommodating the detection member 20 inside the needle member 10 can be incorporated into the series of steps of manufacturing the needle member 10, and thus, it is possible to make a sensor manufacturing process efficient. Further, the sliding with the inner surface of the needle member 10 is reduced as compared to the case where the detection member 20 is inserted into the needle member 10 after completion of the needle member 10, and thus, it is possible to prevent coating or the like of the detection member 20 from being damaged and peeled off. Meanwhile, the detection member 20 may be inserted inside the needle member 10 after completion of the needle member 10. However, as in the present embodiment for the above-described reason, it is preferable that the detection member 20 be arranged in advance at the stage of being deformed into the tubular shape before completion of the needle member 10 and the step of forming the tubular shape be executed and completed in such a state.

Next, the portion of the joint X of the plate-shaped body 111 deformed into the tubular shape in the tubular shape pressing step S4 is welded or bonded in the joining step S5. In other words, the portion of the joint X of the tubular body obtained in the tubular shape pressing step S4 is welded or bonded by laser processing or the like. Specifically, the outer edges 112 of the plate-shaped body 111 in which the concave portions 113 are formed are aligned to weld the joint X in FIG. 15. Thus, the concave portions 113 formed in the outer edges 112 of the plate-shaped body 111 to be aligned during the deformation into the tubular shape in the tubular shape pressing step S4 form the through-hole 40a in the joining step S5. As a result, it is possible to obtain the cylindrical body 114 in which the through-hole 40a as the opening portion 40 is formed.

Further, the above-described sensor 1 can be created by forming the blade surface portion 115 at one end portion of the cylindrical body 114 using a grindstone, a wire cutter, a laser cutter, or the like in the sharpening step S6.

Although the concave portion formation step S2 is executed after the thickness pressing step S1 in the examples illustrated in FIGS. 13 to 15, the concave portion formation step S2 may be executed before the thickness pressing step S1. That is, the concave portion formation step may be executed on the plate material 110 before providing the thick portion 12a, and the present invention may be executed on the plate-shaped body 111 provided with the thick portion 12a as illustrated in FIGS. 13 to 15.

In addition, the method for manufacturing the sensor 1 illustrated in FIGS. 13 to 15 may include another step such as a cleaning step in addition to the above-described six steps S1 to S6.

Figure 16A:
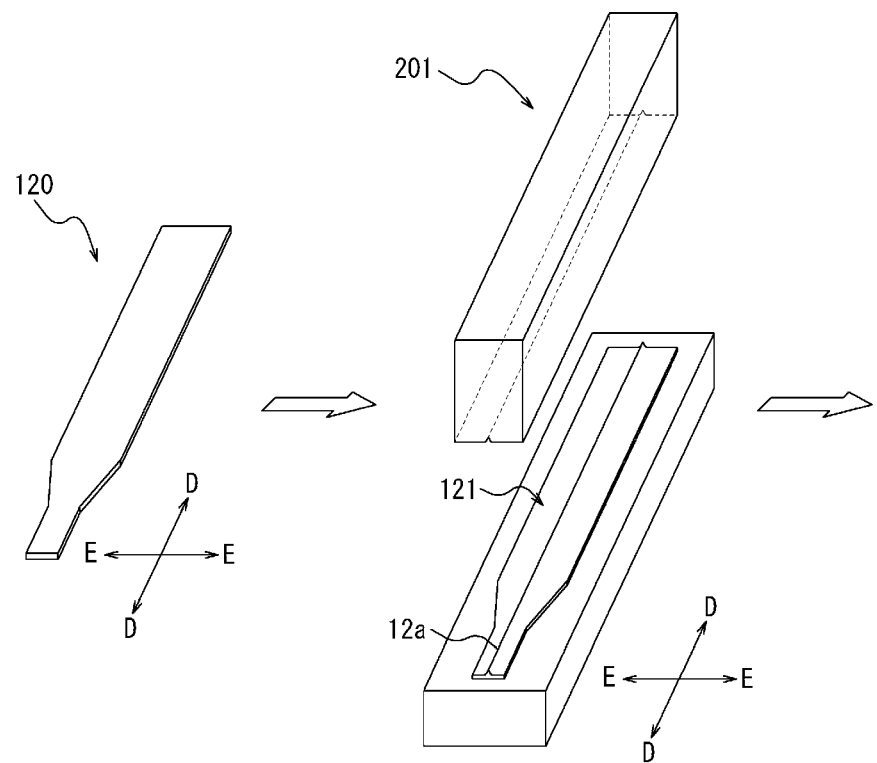
FIG. 16A is a schematic view illustrating an outline of a part of a series of steps in a method for manufacturing the sensor illustrated in FIG. 7.
Figure 16A:
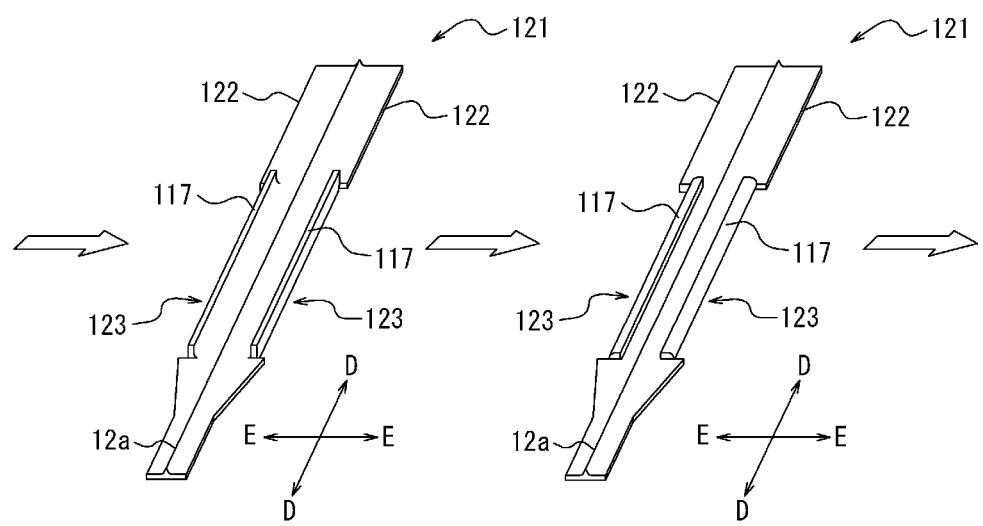
Figure 16B:
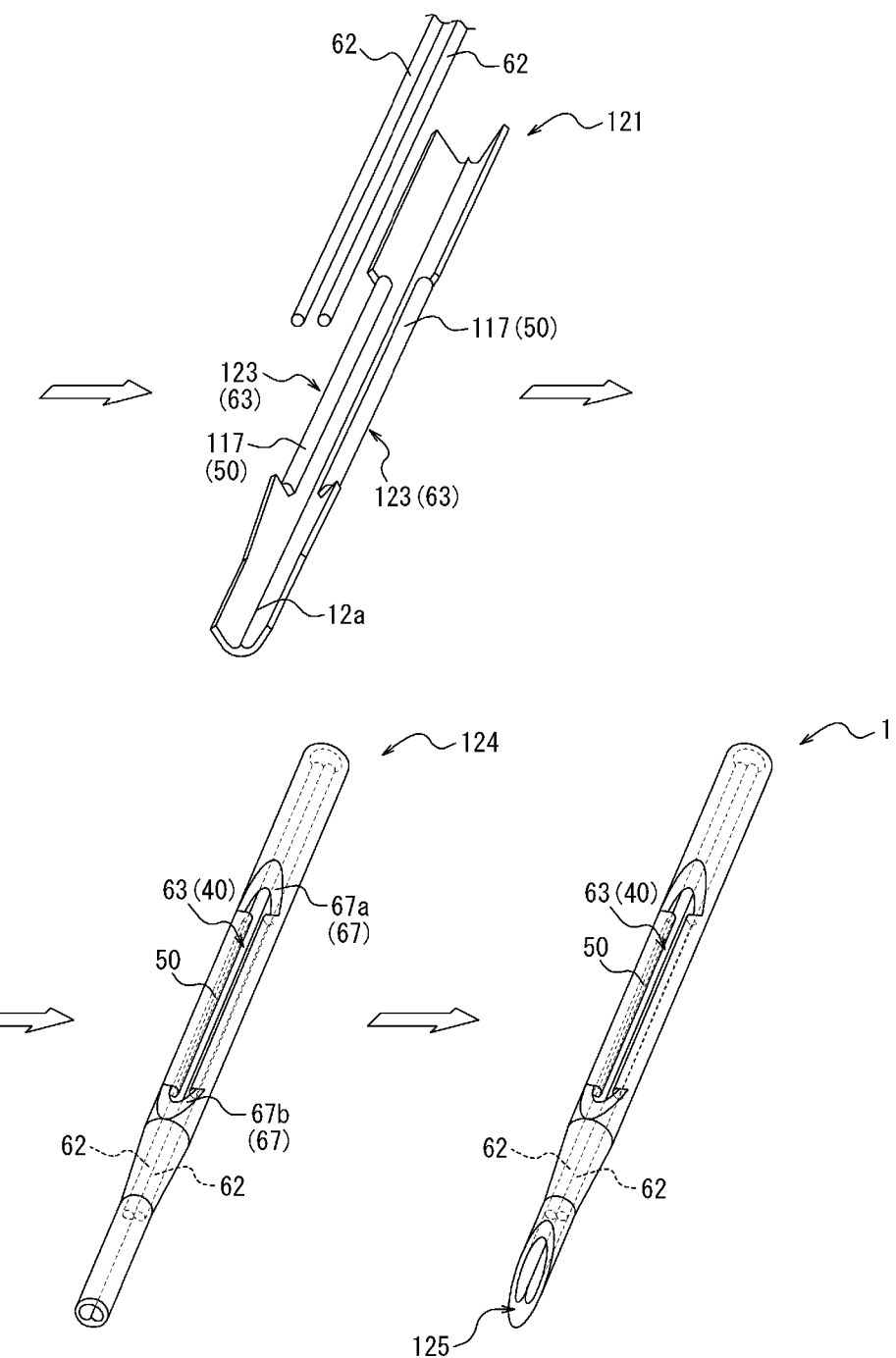
FIG. 16B is a schematic view illustrating an outline of a part of the series of steps in the method for manufacturing the sensor illustrated in FIG. 7.

Next, a method for manufacturing the sensor 60 will be described. As an example of the method for manufacturing the sensor 60, the same method as the method for manufacturing the sensor 1 illustrated in FIG. 13 can be employed. FIGS. 16A and 16B are schematic views illustrating outlines of a series of steps S1 to S6 when the method for manufacturing the sensor 1 illustrated in FIG. 13 is applied as the method for manufacturing the sensor 60. The method for manufacturing the sensor 60 illustrated in FIGS. 16A and 16B includes: a thickness pressing step S1 of pressing a plate material 120 using the first press-molding machine 201 to form a plate-shaped body 121 having the thick portion 12a; a concave portion formation step S2 of forming a concave portion 123 at an outer edge 122 of the plate-shaped body 121; a reception step S3 of receiving the plate-shaped body 121 in which the concave portion 123 has been formed in the second press-molding machine 202; a tubular shape pressing step S4 of pressing the plate-shaped body 121 continuously using the second press-molding machine 202 to be deformed into a tubular shape to form a tubular body; a joining step S5 of welding or bonding a portion of a joint X of the plate-shaped body 121, which has been deformed into the tubular shape, to form a cylindrical body 124; and a sharpening step S6 of forming a blade surface portion 125 at one end portion of the cylindrical body 124. White arrow in FIGS. 16A and 16B represent a temporal change in the steps. Specifically, the outline of the thickness pressing step S1 is illustrated in two drawings depicted on the upper part of FIG. 16A. An outline of the concave portion formation step S2 is illustrated in the two drawings depicted in the lower part of FIG. 16A. The outline of the tubular shape pressing step S4 is illustrated in the drawing depicted on the right of the lower part of FIG. 16A, and the drawing depicted on the upper part and the drawing depicted on the left of the lower part of FIG. 16B. The outline of the joining step S5 is illustrated in the drawing depicted on the left of the lower part of FIG. 16B. The outline of the sharpening step S6 is illustrated in the drawing depicted on the right of the lower part of FIG. 16B. FIGS. 16A and 16B do not depict an upper die and a lower die of the second press-molding machine 202 that is used for the tubular shape pressing step S4. Details of the respective steps S1 to S6 are the same as those of the method for manufacturing the sensor 1 illustrated in FIGS. 13 to 15 described above, and thus, will not be described here. Meanwhile, the method for manufacturing the sensor 60 may include a sloped portion formation step of forming the above-described slope portion 67, for example, in the tubular shape pressing step S4 or after the joining step S5. In the example illustrated here, the slope portion formation step of forming the slope portion 67 is included in the tubular shape pressing step S4.

Figure 17:
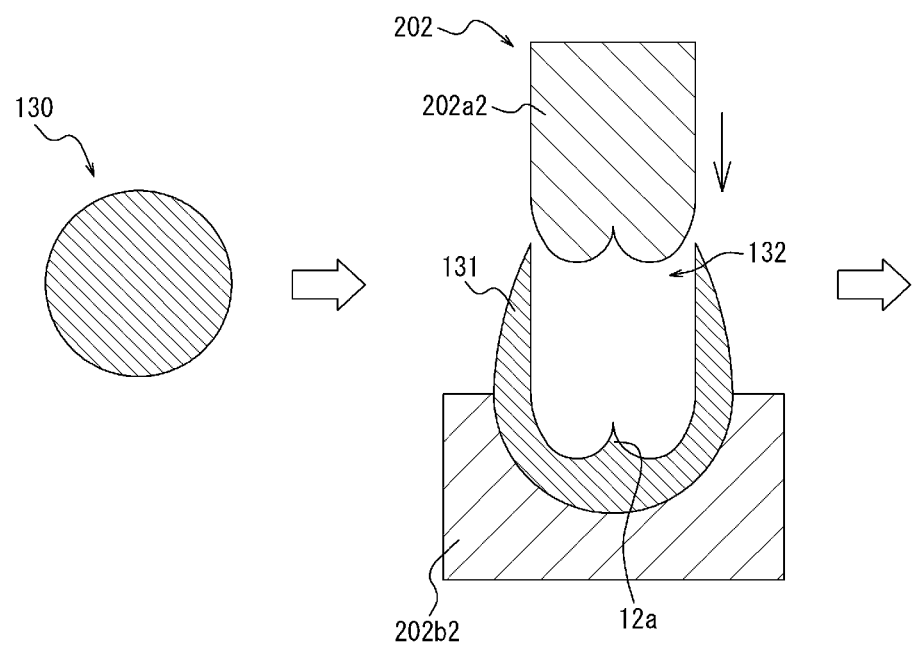
FIG. 17 is a schematic view illustrating an outline of a part of a series of steps in a method for manufacturing the sensor illustrated in FIG. 12.
Figure 17:
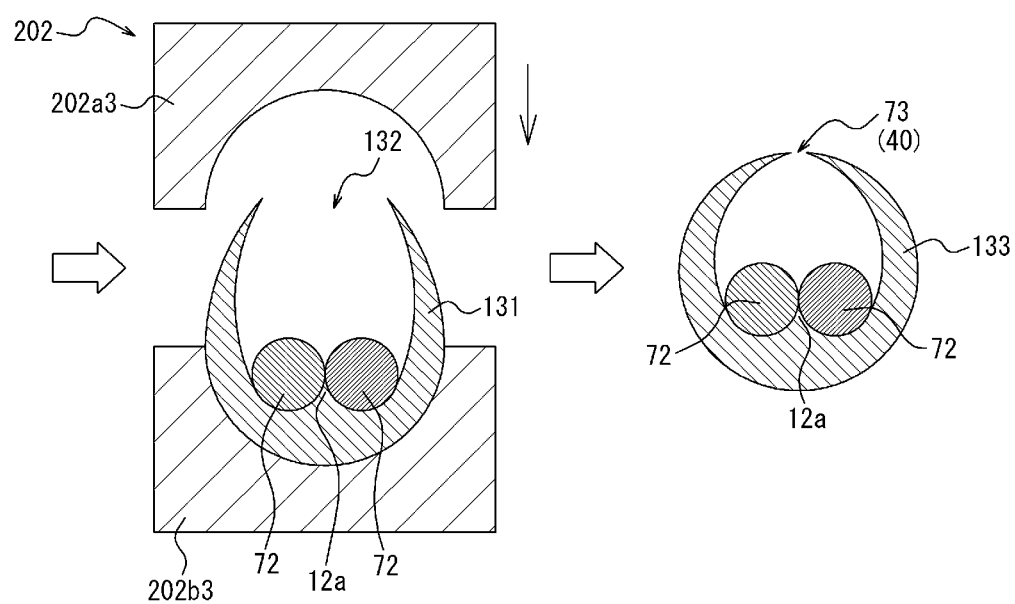

In addition, the above-described sensor 70 can be manufactured by executing the steps S1, S4, and S6 excluding the concave portion formation step S2, the reception step S3, and the joining step S5 in the method for manufacturing the sensor 1 illustrated in FIGS. 13 to 15 Specifically, as illustrated in FIG. 17, the method for manufacturing the sensor 70 includes: a thickness pressing step of forming a semi-tubular body 131 having the thick portion 12a and an open portion 132; a tubular shape pressing step of pressing the semi-tubular body 131 to be deformed into a tubular shape to form a tubular body 133; and the sharpening step S6 of forming the blade surface portion 115. In the sharpening step S6, the blade surface portion 115 is formed at one end portion of the tubular body 133 having a C-shaped cross section instead of the above-described cylindrical body 114 (see FIGS. 14B and 15). In this manner, if the sensor 70 is formed by pressing a rod material 130, it is easy to use the detection member 20 with a smaller diameter and more flexibility as compared to the method for manufacturing the sensor 1 and the sensor 60 described above. Although the detection member 20 is enclosed in the semi-tubular body 131 through the open portion 132 in the tubular shape pressing step of deforming the semi-tubular body 131 into the tubular shape, the detection member 20 may be arranged inside the needle member 71 through the slit 73 or an opening on the proximal end side in the axial direction B after completing the needle member 71 having a substantially C-shaped cross section. Here, the "semi-tubular body" and the "tubular body" mean a relative difference in degree of the tubular shape. Specifically, the "tubular body" means a state closer to a closed complete ring (cylindrical body) than the "semi-tubular body". Although the configuration having a substantially U-shaped cross section is referred as the "semi-tubular body" and the configuration having the substantially C-shaped cross section is referred as the "tubular body" in the example illustrated in FIG. 17, two other states may be referred to as the "semi-tubular body" and the "tubular body" as long as the degree of the tubular shape is different.

The sensor and the method for manufacturing the sensor according to the present disclosure are not limited to the specific configuration and process described in the above embodiments, and various modifications, changes, and combinations can be made without departing from a scope of the claims. The sensor illustrated in the above embodiment has the configuration in which the thick portion is provided in only one point in the circumferential direction A, but may have a configuration in which the thick portion is provided at a plurality of points in the circumferential direction A. In addition, the concave portion 113 serving as the through-hole 40a when the cylindrical body 114 is formed is formed in the plate material 110 or the plate-shaped body 111 in the method for manufacturing the sensor 1 illustrated in the above embodiment, but processing may be performed to form the cylindrical body 114, and then, form the through-hole 40a. In this case, it is preferable to employ a processing method in which heat is not applied to the cylindrical body 114. However, the concave portion 113 that serves as a base of the through-hole 40a can be formed in the series of steps of forming the cylindrical body 114 if the concave portion 113 is formed in the course of forming the cylindrical body 114 as illustrated in the above embodiments. Thus, it is unnecessary to separately execute post-processing only for formation of the through-hole 40a after formation of the cylindrical body 114, and to enhance the work efficiency in the manufacture of the sensor 1.

The present disclosure relates to a sensor and a method for manufacturing the sensor.

REFERENCE NUMERAL LIST 1 sensor
2 control unit
3 support member
4 housing
10 needle member
11 hollow portion
11a distal end opening
12 side wall
12a thick portion
13 thick portion inner wall
13a receiving surface
14 top portion
15 first side portion
16 second side portion
17 blade surface portion
17a blade surface
17b needle tip
17c heel portion
18 edge portion
19 receiving groove
20 detection member
20a first detection member
20b second detection member
40 opening portion
40a through-hole
50 opening reinforcement portion
60 sensor
61 needle member
61a body portion
61b distal end portion
61c tapered portion
62 detection member
63 through-hole
64 edge portion
65 blade surface portion
66a side wall of body portion
66b side wall of distal end portion
66c side wall of tapered portion
67 slope portion
67a first slope portion
67b second slope portion
70 sensor
71 needle member
72 detection member
73 slit
74 side wall
75 edge portion
100 measurement device
110 plate material
111 plate-shaped body
112 outer edge of plate-shaped body
113 concave portion
114 cylindrical body
115 blade surface portion
116 notch
117 bending piece
120 plate material
121 plate-shaped body
122 outer edge
123 concave portion
124 cylindrical body
125 blade surface portion
130 rod material
131 semi-tubular body
132 open portion
133 tubular body
201 first press-molding machine
202 second press-molding machine
202a1 first upper die
202a2 second upper die
202a3 third upper die
202b1 first lower die
202b2 second lower die
202b3 third lower die A circumferential direction of needle member
B axial direction of needle member
C radial direction of needle member
D longitudinal direction of plate material and plate-shaped body
E lateral direction of plate material and plate-shaped body
O central axis of needle member
X joint
BS body surface of subject

The invention claimed is:

1. A sensor comprising:
a tubular needle member that comprises a side wall and defines a hollow portion; and
a linear detection member located in and immovably fixed in the hollow portion; wherein:
the side wall of the needle member comprises a thick portion that is thicker than another portion of the side wall in a cross-section of the needle member, and wherein the thick portion protrudes toward the hollow portion;
the thick portion comprises a thick portion inner wall, and the thick portion inner wall comprises a receiving surface that receives the detection member;
the thick portion inner wall further comprises:
a top portion, a first side portion that is continuous from the top portion to a first side of the needle member in a circumferential direction and in which a wall thickness of the needle member gradually decreases from the top portion toward the first side of the needle member in the circumferential direction, and
a second side portion that is continuous from the top portion to a second side of the needle member in the circumferential direction and in which the wall thickness of the needle member gradually decreases from the top portion toward the second side of the needle member in the circumferential direction; and
the receiving surface is a surface of at least one of the first side portion or the second side portion.

2. The sensor according to claim 1, wherein:
the receiving surface has a receiving shape corresponding to an outer shape of the detection member, and the receiving surface extends along a portion of an outer surface of the detection member in a cross-section of the sensor.

3. The sensor according to claim 1, wherein:
the detection member has a substantially circular outer shape in cross section; and
the receiving surface comprises a concave curved surface that receives the detection member.

4. The sensor according to claim 1, wherein:
the detection member is a first detection member;
the receiving surface is a first receiving surface;
the sensor further comprises a second linear detection member located in the hollow portion; and
the thick portion inner wall further comprises a second receiving surface that receives the second detection member.

5. The sensor according to claim 1, wherein:
the side wall of the needle member further comprises an opening portion that comprises a through-hole or a slit.

6. The sensor according to claim 5, wherein:
the side wall of the needle member further comprises an opening reinforcement portion extending along an edge portion of the side wall that defines the opening portion.

7. The sensor according to claim 5, wherein:
the opening portion opposes the thick portion in a radial direction of the needle member.

8. The sensor according to claim 1, wherein:
the needle member further comprises, at a distal end portion, a blade surface portion comprising:
a blade surface that is inclined with respect to an axial direction of a central axis of the needle member, and
a needle tip that is a distal end of the blade surface;
the blade surface defines a distal end opening;
the thick portion extends to the distal end opening; and
the thick portion is formed at a position where a line segment connecting a central axis of the needle member and the needle tip intersects the side wall in a plan view in which the needle member is viewed from a distal end side.

9. The sensor according to claim 1, wherein the linear detection member is fixed in the hollow portion by an adhesive.

10. A sensor comprising:
a tubular needle member that comprises a side wall and defines a hollow portion; and
a linear detection member located in the hollow portion; wherein:
the side wall of the needle member comprises a thick portion that is thicker than another portion of the side wall in a cross-section of the needle member, and wherein the thick portion protrudes toward the hollow portion;
the thick portion comprises a thick portion inner wall, and the thick portion inner wall comprises a receiving surface that receives the detection member; and
the thick portion inner wall further comprises:
a top portion, a first side portion that is continuous from the top portion to a first side of the needle member in a circumferential direction and in which a wall thickness of the needle member gradually decreases from the top portion toward the first side of the needle member in the circumferential direction, and
a second side portion that is continuous from the top portion to a second side of the needle member in the circumferential direction and in which the wall thickness of the needle member gradually decreases from the top portion toward the second side of the needle member in the circumferential direction; and
the receiving surface is a surface of at least one of the first side portion or the second side portion.

* * * * *